(12) United States Patent
Nistor et al.

(10) Patent No.: US 9,820,934 B2
(45) Date of Patent: Nov. 21, 2017

(54) ACID CONTAINING LIPID FORMULATIONS

(75) Inventors: Catalin Nistor, Lund (SE); Markus Johnsson, Lund (SE); Fredrik Tiberg, Lund (SE)

(73) Assignee: CAMURUS AB (SE)

( * ) Notice: Subject to any disclaimer, the term of this patent is extended or adjusted under 35 U.S.C. 154(b) by 1328 days.

(21) Appl. No.: 12/674,226

(22) PCT Filed: Aug. 22, 2008

(86) PCT No.: PCT/GB2008/002857
§ 371 (c)(1),
(2), (4) Date: Jun. 2, 2011

(87) PCT Pub. No.: WO2009/024795
PCT Pub. Date: Feb. 26, 2009

(65) Prior Publication Data
US 2012/0028890 A1 Feb. 2, 2012

(30) Foreign Application Priority Data

Aug. 22, 2007 (GB) .................................. 0716385.0

(51) Int. Cl.
*A61K 9/00* (2006.01)
*A61K 9/06* (2006.01)
*A61K 9/127* (2006.01)
*A61K 38/26* (2006.01)
*A61K 47/10* (2017.01)
*A61K 47/14* (2017.01)
*A61K 47/24* (2006.01)

(52) U.S. Cl.
CPC .............. *A61K 9/0019* (2013.01); *A61K 9/06* (2013.01); *A61K 9/127* (2013.01); *A61K 9/1274* (2013.01); *A61K 38/26* (2013.01); *A61K 47/10* (2013.01); *A61K 47/14* (2013.01); *A61K 47/24* (2013.01)

(58) Field of Classification Search
CPC ....... A61K 38/26; A61K 47/20; C07K 14/605
See application file for complete search history.

(56) References Cited

U.S. PATENT DOCUMENTS

| | | | |
|---|---|---|---|
| 4,938,763 A | 7/1990 | Dunn et al. | |
| 5,340,802 A | 8/1994 | Shiosaki et al. | |
| 5,480,656 A | 1/1996 | Okada et al. | |
| 5,531,925 A | 7/1996 | Landh et al. | |
| 5,639,480 A | 6/1997 | Bodmer et al. | |
| 5,776,885 A | 7/1998 | Orsolini et al. | |
| 5,807,573 A | 9/1998 | Ljusberg-Wahren et al. | |
| 5,955,502 A | 9/1999 | Hansen et al. | |
| 6,066,328 A | 5/2000 | Ribier et al. | |
| 6,113,943 A | 9/2000 | Okada et al. | |
| 6,228,383 B1 | 5/2001 | Hansen et al. | |
| 6,458,924 B2 | 10/2002 | Knudsen et al. | |
| 6,464,987 B1 | 10/2002 | Fanara et al. | |
| 8,097,239 B2 | 1/2012 | Johnsson et al. | |
| 8,182,834 B2 | 5/2012 | Johnsson et al. | |
| 8,187,629 B2 | 5/2012 | Barauskas et al. | |
| 8,236,292 B2 | 8/2012 | Thuresson et al. | |
| 8,236,755 B2 | 8/2012 | Thuresson et al. | |
| 2002/0026027 A1 | 2/2002 | Ansell | |
| 2002/0102280 A1* | 8/2002 | Anderson | 424/400 |
| 2003/0022242 A1 | 1/2003 | Anderson | |
| 2004/0018241 A1 | 1/2004 | Houze et al. | |
| 2004/0201117 A1 | 10/2004 | Anderson | |
| 2005/0136059 A1 | 6/2005 | Thorpe et al. | |
| 2006/0073203 A1 | 4/2006 | Ljusberg-Wahren et al. | |
| 2007/0080323 A1 | 4/2007 | Joabsson et al. | |
| 2007/0110777 A1 | 5/2007 | Joabsson et al. | |
| 2007/0134336 A1 | 6/2007 | Worle et al. | |
| 2007/0231374 A1 | 10/2007 | Tiberg et al. | |
| 2008/0124394 A1 | 5/2008 | Johnsson et al. | |
| 2008/0146490 A1 | 6/2008 | Joabsson et al. | |
| 2008/0161276 A1 | 7/2008 | Johnsson et al. | |
| 2008/0214995 A1 | 9/2008 | Boyd et al. | |
| 2008/0274176 A1 | 11/2008 | Johnsson et al. | |
| 2009/0069221 A1 | 3/2009 | Joabsson et al. | |
| 2009/0155193 A1 | 6/2009 | Joabsson et al. | |
| 2009/0170782 A1 | 7/2009 | Joabsson et al. | |

(Continued)

FOREIGN PATENT DOCUMENTS

| EP | 1600162 | 11/2005 |
|---|---|---|
| WO | WO 93/06921 A1 | 4/1993 |

(Continued)

OTHER PUBLICATIONS

L. M. Knudsen et al., "Potent Derivatives of Glucagon-like Peptide-1 with Pharmacokinetic Properties Suitable for Once Daily Administration", J. Med. Chem. (2000) vol. 43, pp. 1664-1669.

G. G. Holz et al., "Glucagon-Like Peptide-1 Synthetic Analogs: New Therapeutic Agents for Use in the Treatment of Diabetes Mellitus", Current Medicinal Chemistry (2003), vol. 10, pp. 2471-2483.

H. Hui et al., "Structure and function studies of glucagon-like peptide-1 (GLP-1): the designing of a novelpharmacological agent for the treatment of diabetes", Diabetes Metabolism Research and Reviews, (2005), vol. 21, pp. 313-331.

L. M. Knudsen, "Glucagon-like Peptide-1: The Basis of a New Class of Treatment for Type 2 Diabetes", J. Med. Chem. (2004), vol. 47, pp. 4128-4134.

About Sandostatin: Proven Control of GH, 1GF-1 and Gastrointestinal Hormone, from www.sandostatin.com/about.sandostatin/index.html and linked documents.

(Continued)

*Primary Examiner* — Abigail Vanhorn
*Assistant Examiner* — Jessica Kassa
(74) *Attorney, Agent, or Firm* — J.A. Lindeman & Co., PLLC

(57) ABSTRACT

The present invention relates to compositions forming a low viscosity mixture of: i) a non-polymeric slow-release matrix ii) at least one biocompatible, (preferably oxygen containing) organic solvent; iii) at least one peptide active agent; and iv) at least one lipid soluble acid. The invention further relates to methods of treatment comprising administration of such compositions, especially in treating diabetes, and to pre-filled administration devices and kits containing the formulations.

25 Claims, 2 Drawing Sheets

(56) References Cited

U.S. PATENT DOCUMENTS

| | | | |
|---|---|---|---|
| 2010/0210519 A1 | 8/2010 | Johnsson et al. | |
| 2011/0230569 A1 | 9/2011 | Nistor et al. | |
| 2012/0269772 A1 | 10/2012 | Thuresson et al. | |

FOREIGN PATENT DOCUMENTS

| | | | |
|---|---|---|---|
| WO | WO 95/34287 A1 | 12/1995 | |
| WO | WO 97/13528 A1 | 4/1997 | |
| WO | WO 98/47487 A1 | 10/1998 | |
| WO | WO 02/02716 A2 | 1/2002 | |
| WO | WO 02/066014 A2 | 8/2002 | |
| WO | WO 02/068561 A2 | 9/2002 | |
| WO | WO 02/068562 A2 | 9/2002 | |
| WO | WO 03/002136 A1 | 1/2003 | |
| WO | WO 03/057235 A2 | 7/2003 | |
| WO | WO 2004/087215 A1 | 10/2004 | |
| WO | WO 2005/014162 A1 | 2/2005 | |
| WO | WO 2005/021022 A2 | 3/2005 | |
| WO | 2005/046642 A1 | 5/2005 | |
| WO | WO 2005/048952 A2 | 6/2005 | |
| WO | WO 2005/063213 A1 | 7/2005 | |
| WO | WO 2005/070394 A2 | 8/2005 | |
| WO | 2005/117830 A1 | 12/2005 | |
| WO | WO 2006/075123 A1 | 7/2006 | |
| WO | WO 2006/075124 A1 | 7/2006 | |
| WO | WO 2006/075125 A1 | 7/2006 | |
| WO | WO 2006/077362 A1 | 7/2006 | |
| WO | 2006/131730 A1 | 12/2006 | |
| WO | WO 2008/152401 A1 | 12/2008 | |
| WO | WO 2009/024795 A1 | 2/2009 | |
| WO | WO 2009/024797 A1 | 2/2009 | |
| WO | WO 2010/020794 A1 | 2/2010 | |

OTHER PUBLICATIONS

"Acromegaly" from www.niddk.nil.gov/health/endo/pubs/acro/acro.htm.
American Peptide Company, Product Details "Somatostatin and analogs," from www.americanpeptide.com/.
N. Ardjomand et al., "Expression of Somatostatin Receptors in uveal melanomas," Inv. Opthalmol. & Vis. Sci., 2003, vol. 44, No. 3, pp. 980-987.
Barauskas et al., Pharmaceutical Nanotechnology, "Interactions of lipid-based liquid crystalline nanoparticles with model and cell membranes," International Journal of Pharmaceutics 391 (2010) pp. 284-291.
R. Berges, "Eligard: Pharmacokinetics, Effect on Testosterone and PSA Levels and Tolerability," European Urology Supplements, 2005, vol. 4, pp. 20-25.
Chang, J., "Use of GnRH agonists in the treatment of hyperandrogenism and hirsutism," print out from http://patients.uptodate.com.
P. Chanson et al., "Comparison of octreotide acetate LAR and lanreptide SR in patients with acromegaly," Clin. Endocrinology, 2001, vol. 54, No. 1, pp. 11-13, (Abstract only).
Comets et al., "Non parametric analysis of the absorption profile of octreotide in rabbits from long-acting release formulation OncoLAR," J. Controlled Release 59:197-205 (1999).
F. Dall'Antonia, "Structure determination of organo-silicon compounds.", pp. 6 to 8 from http://shelx.uni-ac.gwdg.de/-fabio/endwkcon.htm.
Definition of analog from http://cancerweb.ncl.ac.uk!omd/about.html, pp. 1-5. Accessed Jul. 7, 2005.
B. L. Erstad, "Octreotide for acute variceal bleeding," Ann. Pharmacother., 2001, vol. 35, No. 5, pp. 618-626. (Abstract only).
FDA's 510(k) Summary of Camurus AB, episil® K101769.
A. K. Flogstad et al., "Sandostatin LAR in acromegalic patients: long term treatment," J. Clinical Endocrinology & Metabolism, 1997, vol. 82, No. 1, pp. 23-28.
P. R. Gibson & J. G. Muir, "Reinforcing the mucus: a new therapeutic approach for ulcerative colitis," Gut, 2005, vol. 54, pp. 900-903.

L. M. Grant & F. Tibert, "Normal and Lateral Forces between Lipid Covered Solids in Solution: Correlation with Layer Packing and Structure," Biophysical Journal, 2002, vol. 82, pp. 1373-1385.
B.A. Hills, "Surface-active phospholipid: a Pandora's box of clinical applications. Part II. Barrier and lubricating properties," Internal Medicine Journal, 2002, vol. 32, pp. 242-251.
Indications and Usage of Eligard, pp. 1-5, print out from http:ffw-ww.rxlist.com.
Information About Buprenorphine Therapy, print out from http://buprenorphine.samhsa.gov/about.html, pp. 1-4.
Information on Goserelin Acetate print out form http://www.bachem.com/.
Information on Goserelin Subcutaneous, Monograph—Goserelin Acetate, pp. 1-7, print out form www.medscape.com.
Information on Leuprolide Intramuscular, Monograph—Leuprolide Acetate, pp. 1-20, print out for www.medscape.com.
Information on Leuprolide (3 Month) Intramuscular, Monograph—Leuprolide Acetate, pp. 1-20, print out from www.medscape .com.
Invitrogen, "Pluronic F-127," Molecular Probes Invitrogen Detection Technologies, pp. 1-2, 2008.
Johnsson et al., "Physicochemical and Drug Delivery Aspects of Lipid-Based Liquid Crystalline Nanoparticles: A Case Study of Intravenously Administered Propofol," Journal of Nanoscience and Nanotechnology, vol. 6, No. 9/10, pp. 3017-3024, 2006.
Kamo, et al., "Nonlamellar Liquid Crystalline Phases and Their Particle Formation in the Egg Yolk Phosphatidylcholine/Diolein System," Langmuir, vol. 19, pp. 9191-9195, Published on Web Oct. 1, 2003.
Kesisoglou, et al., "Liposomal Formulations of Inflammatory Bowel Disease Drugs: Local versus Systemic Drug Delivery in a Rat Model," Pharmaceutical Research, vol. 22, No. 8, Aug. 2005, pp. 1320-1329.
J. G. M. Klijn et al., "Combined tamoxifen and luteinizing hormone-releasing hormone (LHRH) agonist versus LHRH agonist alone in premenopausal advanced breast cancer: A meta-analysis of four randomized trials," Journal of Clinical Oncology, 2001, vol. 19, No. 2, pp. 343-353 (Abstract only).
I. Lancranjan et al., "Sandostatin LAR: Pharmacokinetics. Pharmacodynamics, Efficacy and Tolerability in Acromegalic Patients," Metabolism, 1995, vol. 44, No. 1, pp. 18-26.
"Leutinizing Hormone Releasing Hormone (LHRH) Agonists: Goserelin (Zoladex) vs. Leuprolide (Lupron) for Prostate Cancer," DoD Pharmacoeconomic Center Update, Newsletter, Dec. 2000, vol. 1, No. 1, print out from http://www.pec.ha.osd.mil.com, pp. 1-3.
Loughrey et al., "Development of a Sensitive Sandwich ELISA for Detecting Full Length Biologically Active TH0318, a GLP-1 Analogue," presented at the 2005 AAPS Annual Meeting and Exposition, Abstract No. W5009.
Martel et al., "Enzyme Linked Immunosorbent Assay (EUSA) Method for the Determination of TH0318, a New GLP-1 Analogue in Development for Diabetes," presented at the 2005 MPS Annual Meeting and Exposition, Abstract No. W5008.
Martel et al., "Enzyme Linked !mmunosorbent Assay (EUSA) Method for the Determination of TH0318, a New GLP-1 Analogue in Development for Diabetes," Poster.
MSDS for Ethylene Glycol and Abbreviations used in Toxicity data.
Novartis Pharmaceuticals Corporation, "Sansdostatin LAR Depot (octreotide acetate for injectable suspension)", pp. 1-19.
PDR Information on Eligard 30 mg (Sanofi-Synthelabo), print out from www.Drugs.com, pp. 1-14.
Pharmaceutical Information on Lupron Depot, print out from www.rxmed.com, pp. 1-8.
Product Information on Zoladex Goserelin Acetate Implant (Equivalent to 10.8 mg goserelin).
Product Specification of Leuprolide by GL Biochem, print out from http://www.glschina.com.
Published Data Provided by Sandostatin LAR "The Latest Research and Treatment Information for Pituitary Disorders" from http://www.sandostatin.com/published data/index.html.
O. Sartor "Eligard: Leuprolide Acetate in a Novel Sustained-Release Delivery System," Urology, 2003, vol. 61, (Supplement 2A), pp. 25-31.

(56) References Cited

OTHER PUBLICATIONS

K. J. Schuh et al., "Onset, magnitude and duration of opioid blockade produced by buprenorphine and naltrexone in humans," Psychopharmacology, (Berl), Jul. 1999, vol. 145, No. 2, pp. 162-174 (Abstract only).
J. C. Shah et al., "Cubic phase gels as drug delivery systems," Advanced Drug Delivery Reviews, 2001, vol. 47, pp. 229-250.
"Setting new standards of care," Mixing and Administration instructions for Sandostatin LAR.
W. Stremmel et al., "Retarded release phosphatidylcholine benefits patients with chronic active ulcerative colitis," Gut, 2005, vol. 54, pp. 966-971.
A Sturm & A. U. Dignass, "Modulation of gastrointestinal wound repair and inflammation by phospholipids," Biochimica et Biophysica Acta, 2002, vol. 1582, pp. 282-288.
Svanberg et al., "A New Preventive Strategy Using a Bioadhesive Oromucosal Lipid Solution and Oral Cryotherapy to Protect the Oral Cavity—and Reduce the Need for Total Parenteral Nutrition (Tpn) for Patients Undergoing Autologous Stemcell Transplantation," Support Care Cancer 18 (Suppl 3):S114-S115, at Abstract 08-076 (2010) (attached hereto as Annex 5 to Evidentiary Declaration Under 37 C.F.R. § 1.132 of Fredrik Tiberg).
Tiberg et al., "Drug delivery applications of non-lamellar liquid crystalline phases and nanoparticles", J. Drug Del Sci. Tech., 21(1) pp. 101-109, 2011.
Tiberg et al., "Treatment of oral mucositis pain by a bioadhesive barrier forming lipid solution," Camurus (attached hereto as Annex 3 to Evidentiary Declaration Under 37 C.F.R. § 1.132 of Fredrik Tiberg).
Tiberg et al., "Treatment of Oral Mucositis Pain by a Bioadhesive Barrier Forming Lipid Solution," Support Care Center 17(7):918 (2009) (attached hereto as Annex 4 to Evidentiary Declaration Under 37 C.F.R. § 1.132 of Fredrik Tiberg).
Treating Acromegaly, from http://www.sandostatin.com/Ireating acromegaly/index.html and linked documents.
Welin et al., "High-dose treatment with a long-acting somatostatin analogue in patients with advanced midgut carcinoid tumours," 2004, Society of the European Journal of Endocrinology, vol. 151, pp. 107-112.
Wermuth, Pure and Appl. Chem, 1998, 70, 1129-1143.
E. Woltering et al., "Octreotide acetate (LAR) dose effect on plasma octreotide levels: Impact on neuroendocrine tumor Management," F. Clin Oncology, 2005 ASCO Annual Meeting Proceedings, vol. 23, No. 16S, pp. 3177 (Abstract only).
E. A. Woltering, "A discussion on the utility of various routes of administration of octreotide acetate," from http://www.carcinoid.org/medpro/docs/WoltPump2005.htm.
International Search Report of PCT/GB2005/004745 dated May 8, 2006.
International Preliminary Report on Patentability of PCT/GB2005/004745 dated Jul. 20, 2007.
Written Opinion of PCT/GB2005/004745 dated May 8, 2006.
International Search Report of PCT/GB2005/04748 dated Mar. 23, 2006.
International Preliminary Report on Patentability of PCT/GB2005/04748 dated Mar. 12, 2007.
Written Opinion of PCT/GB2005/04748 dated Mar. 23, 2006.
International Search Report of PCT/GB2005/04752 dated Mar. 17, 2006.
International Preliminary Report on Patentability of PCT/GB2005/04752 dated Mar. 12, 2007.
Written Opinion of PCT/GB2005/04752 dated Mar. 17, 2006.
International Search Report of PCT/GB2005/004746 dated Mar. 16, 2006.
International Preliminary Report on Patentability and Written Opinion of PCT/GB2005/004746 dated Jul. 17, 2007.
International Search Report of PCT/GB2006/002079 dated Aug. 25, 2006.
International Preliminary Report on Patentability and Written Opinion of PCT/GB2006/002079 dated Dec. 6, 2007.
International Search Report of PCT/GB2008/002035 dated Oct. 6, 2008.
International Preliminary Report on Patentability of PCT/GB2008/002035 Dec. 17, 2009.
Written Opinion of PCT/GB2008/002035 dated Oct. 6, 2008.
International Search Report of PCT/GB2009/002054 dated Nov. 30, 2009.
International Preliminary Report on Patentability and Written Opinion of PCT/GB2009/002054 dated Feb. 22, 2011.
Office Action in U.S. Appl. No. 11/795,243 dated May 12, 2011.
Office Action in U.S. Appl. No. 11/795,243 dated Mar. 22, 2012.
Office Action in U.S. Appl. No. 11/795,249 dated Jul. 19, 2011.
Office Action in U.S. Appl. No. 11/795,249 dated Oct. 25, 2010.
Office Action in U.S. Appl. No. 11/795,250 dated Dec. 21, 2012.
Office Action in U.S. Appl. No. 11/795,250 dated Mar. 18, 2011.
Office Action in U.S. Appl. No. 11/795,250 dated Jun. 24, 2010.
Office Action in U.S. Appl. No. 11/795,242 dated Jan. 10, 2013.
Office Action in U.S. Appl. No. 11/795,242 dated Dec. 23, 2011.
Office Action in U.S. Appl. No. 11/908,740 dated Feb. 14, 2012.
Office Action in U.S. Appl. No. 11/877,935 dated Dec. 21, 2010.
International Search Report of International Application No. PCT/GB2008/002857 dated Dec. 8, 2008.
Written Opinion of the International Searching Authority of International Application No. PCT/GB2008/002857.
Apr. 23, 2014, Office Action in U.S. Appl. No. 11/795,243.
Office Action in U.S. Appl. No. 11/795,249 dated Dec. 4, 2013.
Office Action in U.S. Appl. No. 11/795,250 dated Dec. 4, 2013.
Office Action in U.S. Appl. No. 12/664,835 dated Oct. 25, 2013.

* cited by examiner

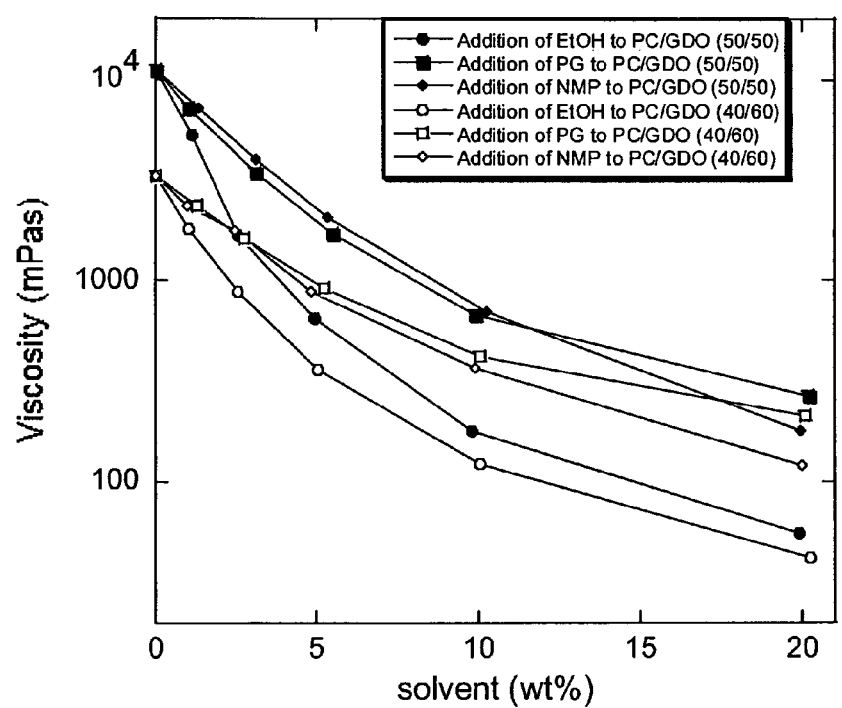
Figure 1. Decrease in viscosity at 25 °C of the depot precursor on addition of solvents. PC/GDO (5/5) is a precursor to a reversed hexagonal $H_{II}$ phase and PC/GDO (4/6) is a precursor to a reversed cubic $I_2$ phase.

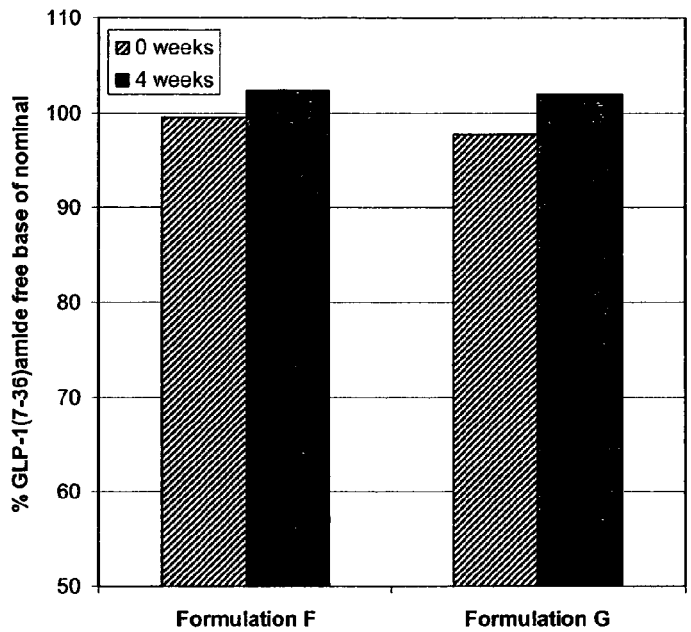
*Figure 2.* Assayed (HPLC) GLP-1 free base content (expressed as % of nominal content) in Formulation F and G (Table 4) after 0 and 4 weeks storage at 5°C.
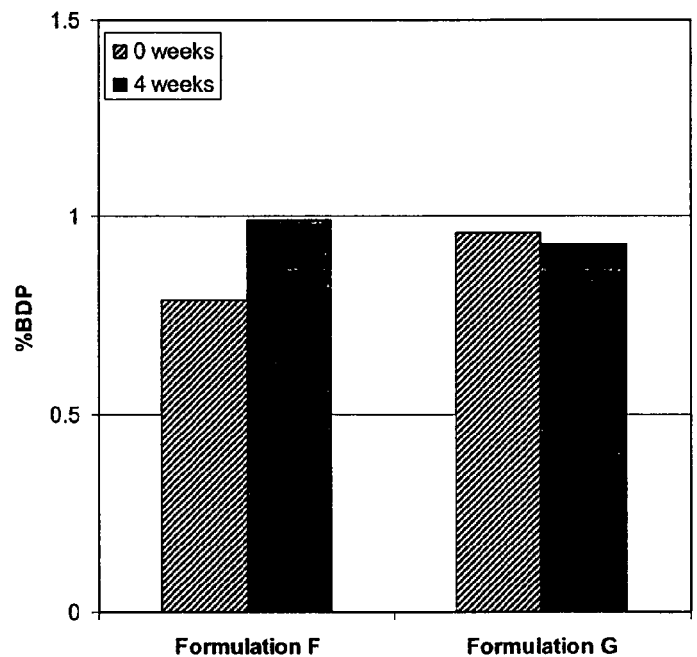
*Figure 3.* Assayed (by % Total Area at 214 nm) Break Down Products (BDPs) in Formulation F and G (Table 4) after 0 and 4 weeks storage at 5°C.

ACID CONTAINING LIPID FORMULATIONS

The present invention relates to formulation precursors (pre-formulations) for the in situ generation compositions for the controlled release of peptide active agents such as Glucagon-like-peptide-1 (GLP-1) and/or analogues thereof, and methods of treatment with such formulations. In particular, the invention relates to high-loading pre-formulations of amphiphilic components and at least one GLP-1 or analogues active agent for parenteral application, which undergo phase transition upon exposure to aqueous fluids, such as body fluids, thereby forming a controlled release matrix.

Many bioactive agents including pharmaceuticals, nutrients, vitamins and so forth have a "functional window". That is to say that there is a range of concentrations over which these agents can be observed to provide some biological effect. Where the concentration in the appropriate part of the body (e.g. locally or as demonstrated by serum concentration) falls below a certain level, no beneficial effect can be attributed to the agent. Similarly, there is generally an upper concentration level above which no further benefit is derived by increasing the concentration. In some cases increasing the concentration above a particular level results in undesirable or even dangerous effects.

Some bioactive agents have a long biological half-life and/or a wide functional window and thus may be administered occasionally, maintaining a functional biological concentration over a substantial period of time (e.g. 6 hours to several days). In other cases the rate of clearance is high and/or the functional window is narrow and thus to maintain a biological concentration within this window regular (or even continuous) doses of a small amount are required. This can be particularly difficult where non-oral routes of administration (e.g. parenteral administration) are desirable or necessary, since self-administration may be difficult and thus cause inconvenience and/or poor compliance. In such cases it would be advantageous for a single administration to provide active agent at a therapeutic level over the whole period during which activity is needed.

There is an enormous potential in the use of peptides (including proteins) for treating various disease states, as well as in prophylaxis and in improving general health and wellbeing of subjects. However, the performance of administered peptide agents is generally limited due to poor bioavailability, which in turn is caused by the rapid degradation of peptides and proteins in biological fluids. This increases the dose which must be administered and in many cases restricts the effective routes of administration. These effects are further exaggerated by the often limited permeability of peptides and proteins across biological membranes.

Peptides and proteins that are administered to the mammalian body (e.g. orally, intramuscularly etc.) are subject to degradation by various proteolytic enzymes and systems present throughout the body. Well known sites of peptidase activity include the stomach (e.g. pepsin), and the intestinal tract (e.g. trypsin, chymotrypsin, and others) but other peptidases (e.g. the carboxypeptidases A, B & C) are found throughout the body. Upon oral administration, gastric and intestinal degradation reduces the amount of peptide or protein which potentially could be absorbed through the intestinal surface lining and thereby decrease their bioavailability. Similarly, free peptides and proteins in the mammalian blood stream are also subject to enzymatic degradation (e.g. by plasma carboxy peptidases etc.).

There are many peptide based active agents, some of which are discussed herein below. Among these, one of particular interest is GLP-1.

Glucagon-like peptide (GLP)-1 is a potent glucoregulatory hormone that is released from intestinal L cells into the circulation in response to nutrient ingestion and neural and endocrine stimuli. Structurally, GLP-1 precursor (precursor to the active forms) is a 37-amino acid peptide with a MW of 4.2 KDa, having a sequence highly conserved between different species. After post-translational cleavage of the first six amino acids of the precursor, two equipotent active forms of GLP-1 ((7-37) and (7-36)amide) are generated. GLP-1 is involved in modification of glucose homeostasis through actions that include potentiation of glucose-stimulated insulin secretion and biosynthesis and suppression of glucagon secretion, gastric emptying, and food intake. The abilities of GLP-1 to stimulate insulin secretion and inhibit glucagon release are glucose-dependent; thus, the risk of hypoglycemia with GLP-1 administration is low. GLP-1 also increases beta-cell mass in preclinical models of diabetes through mechanisms that include stimulation of beta-cell proliferation and neogenesis and inhibition of beta-cell apoptosis. Studies in both animals and humans indicate that GLP-1 may also play a protective role in the cardiovascular system.

The combined actions of GLP-1 have generated substantial interest in using this peptide as a therapeutic agent for the treatment metabolic diseases, including type II diabetes and obesity. However, the therapeutic potential of native GLP-1 is limited by its very short plasma half-life (below 2 minutes). This is due to both rapid inactivation by the proteolytic enzyme dipeptidyl peptidase (DPP)-IV and renal clearance. Consequently, long-acting, DPP-IV-resistant GLP-1 analogues have been developed for clinical use, including exenatide (Byetta, Amylin-Lilly), liraglutide (Novo Nordisk), CJC-1131 (ConjuChem), AVE010 (Zealand Pharma—Sanofi-Aventis), LY548806 (Lilly), TH-0318 (TheraTechnologies), BIM 51077 (Ipsen-Roche). All these are once- or twice-daily administration products; a controlled-release (one week) exenatide product (Exenatide LAR Alkermes-Amylin-Lilly) is currently under clinical investigation. These GLP-1 mimetics bind to GLP-1 receptors with similar or higher affinity and produce biological actions identical to those of native GLP-1 but are resistant to DPP-IV-Mediated inactivation and renal clearance. These compounds are able to exert more sustained GLP-1-like activity for longer periods of time in vivo. An alternative therapeutic approach for prolonging the action of native GLP-1 is to inhibit DPP-IV activity, thereby preventing GLP-1 degradation. Several orally active agents that inhibit DPP-IV activity are also being evaluated for the treatment of type II diabetes.

The structures and sequences of GLP-1 and some known analogues are shown below starting with two equipotent naturally occurring forms. A straightforward system is used to describe fragments and analogues of GLP-1. For example, $Arg^{34}$-GLP-1(7-37) designates an analogue of GLP-1 formally derived from GLP-1 precursor by deleting the amino acid residues Nos. 1 to 6 and substituting the naturally occurring amino acid residue in position 34 (Lys) by Arg.

Native (human) GLP-1(7-37):
His$^7$-Ala-Glu-Gly$^{10}$-Thr-Phe-Thr-Ser-Asp$^{15}$-Val-Ser-Ser-Tyr-Leu$^{20}$-Glu-Gly-Gln- Ala-Ala$^{25}$-Lys-Glu-Phe-Ile-Ala$^{30}$-Trp-Leu-Val-Lys-Gly-Arg-Gly$^{37}$ Native (human):
GLP-1(7-36)amide NovoNordisk (Liraglutide)
Arg$^{34}$Lys$^{26}$-(N-ε-(γ-Glu(N-α-hexadecanoyl)))-GLP-1(7-37)

Conjuchem (CJC-1131)
D-Ala$^8$Lys$^{37}$-(2-(2-(2-maleimidopropionamido(ethoxy)ethoxy)acetamide))-GLP-

1(7-37)

Sanofi-Aventis/Zealand (AVE-010 (ZP10))
His-Gly-Glu-Gly-Thr-Phe-Thr-Ser-Asp-Leu-Ser-Lys-Gln-Met-Glu-Glu-Glu-Ala- Val-Arg-Leu-Phe-Ile-Glu-Trp-Leu-Lys-Asn-Gly-Gly-Pro-Ser-Ser-Gly-Ala- Pro-Pro-Ser-Lys-Lys-Lys-Lys-Lys-Lys Eli Lilly (Exenatide)
His$^7$-Gly-Glu-Gly$^{10}$-Thr-Phe-Thr-Ser-Asp$^{15}$-Leu-Ser-Lys-Gln-Met$^{20}$-Glu-Glu-Glu- Ala-Val$^{25}$-Arg-Leu-Phe-Ile-Glu$^{30}$-Trp-Leu-Lys-Asn-Gly-Gly-Pro$^{37}$-Ser-Ser-Gly- Ala-Pro-Pro-Pro-Ser-amide As used herein, "native GLP-1" indicates human GLP-1 (7-37) and/or human GLP-1 (7-36)amide and the terms "Liraglutide", "CJC-1131", "AVE-010", "exenatide" are used to indicate the respective actives above, including their physiologically acceptable salts, esters and derivatives where context allows. All of these, including the native GLP-1 sequences are included in the term "GLP-1 analogues" as used herein. Other suitable GLP-1 analogues are described in e.g. Knudsen et al. *J. Med. Chem.* 2000, 43, 1664-1669; Knudsen *J. Med. Chem.* 2004, 47, 4128-4134; Hui et al. *Diabetes Metab. Res. Rev.* 2005, 21, 313-331 and Holz and Chepurny *Curr. Med. Chem.* 2003, 10, 2471-2483. These citations are incorporated herein by reference in their entireties, and although specific passages are referred to herein, all GLP-1 analogue sequences and all GLP-1 receptor agonists referred to in any of these documents are suitable for use in the present invention. GLP-1 receptor agonists as referred to herein includes all GLP-1 analogues as described above and in the references cited above.

With regard to administration, conditions such as type II diabetes are ongoing, and any treatment regime will typically involve long-term, ongoing therapy, for periods of months or years. Currently available GLP-1 therapies are typically injectables which require administration around twice a day for the period of treatment. This will generally be by patient self-administration. Since frequent injection over a long period is not an optimal administration strategy, there is clearly scope for GLP-1 users to benefit from long-acting, sustained formulations, which might be administered much less frequently.

The only long-acting GLP-1 product known to be in development is Exenatide LAR, developed by a collaboration of Alkermes, Amylin and Lilly. This uses the Alkermes Medisorb® delivery system consisting of microspheres of biodegradable polymers. The release system comprises a poly(DL-lactide) (PDLL) polymer microsphere formulation suspended in water, which entraps the GLP-1 analogue exenatide. The loading level of exenatide in Exenatide LAR is typically 0.8 to 2 mg per dose administered weekly. Evidently, since patients undergoing treatment with a GLP-1 receptor agonist will typically require ongoing treatment for many months or years, a depot system allowing loading and controlled release of a larger dose over a longer period would offer a considerable advantage.

Polymer microsphere formulations must generally be administered by means of a sizable needle, typically of 20-gauge or wider. This is necessary as a result of the nature of the polymeric dosing systems used, which are typically polymer suspensions. Evidently, it would be an advantage to provide a system of low viscosity, such as a homogeneous solution, dispersion of fine particles, or L$_2$ phase, which could be administered easily through a narrow needle, thus decreasing the discomfort of the patient during the procedure. In the case of type II diabetes, this ease of administration is particularly significant because most patients will currently be on a self-administration regime. Providing a sustained formulation with a duration of a few days, but which is sufficiently complex to administer that it requires treatment by a healthcare professional will not be an advantage to all patients over twice-daily or daily self-administration, and is likely to be more costly. Providing a formulation which gives sufficiently long duration to justify a visit to a health professional for administration and/or a preparation which can be self-administered, and reducing preparation time of health-care professionals or patients prior to the actual administration are all important issues.

The poly-lactate, poly-glycolate and poly-lactate-co-glycolate polymers typically used for degrading slow-release formulations, and which are used in the only known GLP-1 sustained release product, are also the cause of some irritation in at least some patients. In particular, these polymers typically contain a certain proportion of acetic acid impurity, which will irritate the injection site on administration. When the polymer then breaks down, lactic acid and glycolic acid are the degradation products so that further irritation is caused. As a result of the combined effects of wide-needle administration and irritant contents, the discomfort at the site of administration and the formation of connective scar tissue are greater than desirable.

From a drug delivery point of view, polymer depot compositions generally have the disadvantage of accepting only relatively low drug loads and having a "burst/lag"

release profile. The nature of the polymeric matrix, especially when applied as a solution or pre-polymer, causes an initial burst of drug release when the composition is first administered. This is followed by a period of low release, while the degradation of the matrix begins, followed finally by an increase in the release rate to the desired sustained profile. This burst/lag release profile can cause the in vivo concentration of active agent to burst above the functional window immediately following administration, and then drop back through the bottom of the functional window during the lag period before reaching a sustained functional concentration for a period of time. Evidently, from a functional and toxicological point of view this burst/lag release profile is undesirable and could be dangerous. It may also limit the equilibrium concentration which can be provided due to the danger of adverse effects at the "peak" point. The presence of a lag phase may furthermore require supplementary dosing with repeat injections during the start-up period of depot treatment in order to maintain a therapeutic dose while the concentrations of active provided from the depot are sub-functional.

Evidently, in the case of GLP-1 analogues, it is important that the "burst" period, immediately after administration, is not so pronounced that it causes hypoglycemia in the subject. GLP-1 is much safer in this respect than insulin, but clinical trials of some GLP-1 analogues have shown hypoglycemic effects with non-sustained release formulations, and the dose injected when a formulation is designed to last for several weeks will be correspondingly higher. It would therefore be a considerable advantage to minimise the immediate "burst" effect upon administration of a GLP-1 analogue composition.

The manufacture of PLGA microbeads and suspensions is additionally a considerable difficulty with certain existing depot systems. In particular, since the beads are particulate, and polymers clog membranes, they cannot generally be sterile-filtered and furthermore, since the PLGA copolymer melts at around 40° C., they cannot be heat-treated for sterility. As a result, a complex manufacturing process must all be conducted under conditions of high sterility.

Further issues with biodegradable polymer microspheres include complex reconstitution prior to injection and limited storage stability, due both to aggregation and degradation of the delivery system and/or active.

An alternative, lipid-based, slow-release composition of GLP-1 and analogues thereof is described in WO2006/131730. This is a highly effective formulation, but the concentration of GLP-1 analogue which can be included in the formulation is limited by the solubility of the (peptide) active agent. Evidently, a higher concentration of active agent allow for the possibility of longer duration depot products, products maintaining a higher systemic concentration, and products having a smaller injection volume, all of which factors are of considerable advantage under appropriate circumstances. It would thus be of considerable value to establish a way by which higher concentrations of GLP-1 or GLP-1 analogues could be included in a lipid-based depot formulation.

The present inventors have now established that by providing a non-aqueous pre-formulation comprising a non-polymeric slow-release vehicle, at least one peptide active agent (such as at least one GLP-1 receptor agonist), at least one lipid soluble acid and a biologically tolerable solvent in a low viscosity phase, such as molecular solution, a pre-formulation may be generated addressing many of the shortfalls of known depot formulations, and which may be applied to provide a GLP-1 receptor agonist depot. In particular, the pre-formulation is easy to manufacture, may be sterile-filtered, has low viscosity (allowing easy and less painful administration typically through a narrow needle), allows a higher level of bioactive agent to be incorporated than has previously been demonstrated (thus potentially allowing a smaller amount of composition to be used), requires shallow injection and/or forms a desired non-lamellar depot composition in vivo having a controllable "burst" or "non-burst" release profile. The compositions are also formed from materials that are non-toxic, biotolerable and biodegradable, which can be administered by i.m., or s.c. and are suitable for self-administration. Evidently, these advantages apply equally to other suitable active agents, and in particular to peptides.

In a first aspect, the present invention thus provides a non-aqueous pre-formulation comprising a low viscosity mixture of:
i) a non-polymeric slow-release matrix
ii) at least one biocompatible, (preferably oxygen containing) organic solvent;
iii) at least one peptide active agent; and
iv) at least one lipid soluble acid;

In one preferred aspect, the peptide active agent is a GLP-1 receptor agonist and the non-polymeric slow-release matrix is a lipid based slow-release matrix. In a second aspect, the invention therefore provides a non-aqueous pre-formulation comprising a low viscosity mixture of:
i) a lipid-based slow-release matrix
ii) at least one biocompatible, (preferably oxygen containing) organic solvent;
iii) at least one peptide active agent, such as a GLP-1 receptor agonist; and
iv) at least one lipid soluble acid;

In a further aspect, the invention provides a non-aqueous pre-formulation comprising a low viscosity mixture of:
a) at least one neutral diacyl lipid and/or a tocopherol;
b) at least one phospholipid;
c) at least one biocompatible, (preferably oxygen containing) organic solvent;
d) at least one peptide active agent, such as a GLP-1 receptor agonist; and
e) at least one lipid soluble acid;
wherein the pre-formulation forms, or is capable of forming, at least one liquid crystalline phase structure upon contact with an aqueous fluid.

In one preferred embodiment, this non-aqueous pre-formulation will comprise a low viscosity mixture of:
a) at least one diacyl glycerol;
b) at least one phosphatidyl choline;
c) at least one oxygen containing organic solvent;
d) at least one peptide active agent, such as a GLP-1 receptor agonist; and
e) at least one lipid soluble acid;
wherein the pre-formulation forms, or is capable of forming, at least one liquid crystalline phase structure upon contact with an aqueous fluid.

Generally, the aqueous fluid will be a body fluid, particularly extra-vascular fluid, extracellular fluid/interstitial fluid or plasma, and the pre-formulation will form a liquid crystalline phase structure when contacted with such a fluid (e.g. in vivo). The pre-formulation of the invention will generally not contain any significant quantity of water prior to administration.

In a further aspect of the invention, there is also provided a method of delivery of a peptide active agent (especially a GLP-1 receptor agonist) to a human or non-human animal (preferably mammalian) body, this method comprising parenterally administering (e.g. i.m. or preferably s.c.) a non-aqueous pre-formulation comprising a low viscosity mixture of:
i) a non-polymeric slow-release matrix
ii) at least one biocompatible, (preferably oxygen containing) organic solvent;
iii) at least one peptide active agent (preferably a GLP-1 receptor agonist); and
iv) at least one lipid soluble acid;

In a preferred aspect, the non-aqueous pre-formulation comprises a low viscosity mixture of as described in a preferred aspect or embodiment described herein.

In a further aspect, the present invention also provides a method for the preparation of a depot composition comprising exposing a non-aqueous pre-formulation comprising a low viscosity mixture of:
i) a non-polymeric slow-release matrix
ii) at least one biocompatible, (preferably oxygen containing) organic solvent;
iii) at least one peptide active agent (preferably a GLP-1 receptor agonist); and
iv) at least one lipid soluble acid; to an aqueous fluid in vivo.

Preferably the pre-formulation administered is a pre-formulation of the present invention as described herein in any of the aspects of the invention.

In a still further aspect the present invention provides a process for the formation of a non-aqueous pre-formulation suitable for the administration of a peptide bioactive agent to a (preferably a human or non-human mammalian) subject, said process comprising forming a low viscosity mixture of
i) a non-polymeric slow-release matrix
ii) at least one biocompatible, (preferably oxygen containing) organic solvent;
and dissolving or dispersing at least one peptide active agent (preferably a GLP-1 receptor agonist); and GLP-1 receptor agonist and at least one lipid soluble acid in the low viscosity mixture, or in at least one of components i) or ii) prior to forming the low viscosity mixture. Preferably the non-aqueous pre-formulation so-formed is a formulation of the invention as described herein, and in particular, component i) preferably comprises a lipid matrix as described herein, especially a lipid matrix comprising components a) and b) as indicated herein. Preferably, the lipid soluble acid component is added prior to addition of the peptide active agent (e.g. GLP-1 receptor agonist) component.

In a yet still further aspect the present invention provides the use of a low viscosity mixture of:
i) a non-polymeric slow-release matrix
ii) at least one biocompatible, (preferably oxygen containing) organic solvent;
iii) at least one peptide active agent (preferably a GLP-1 receptor agonist); and
iv) at least one lipid soluble acid;
in the manufacture of a non-aqueous pre-formulation for use in the sustained administration of said peptide active agent (e.g. GLP-1 receptor agonist). Preferably the pre-formulation is as described in the preferred aspects of the present invention, and may be, for example a low viscosity mixture of:
a) at least one neutral diacyl lipid and/or a tocopherol;
b) at least one phospholipid;
c) at least one biocompatible, (preferably oxygen containing) organic solvent;
d) at least one peptide active agent, such as a GLP-1 receptor agonist; and
e) at least one lipid soluble acid;
wherein said pre-formulation is capable of forming at least one liquid crystalline phase structure upon contact with an aqueous fluid.

The invention also provides the use of a pre-formulation, or depot composition of the invention in therapy, and in the manufacture of a medicament for treatment of an appropriate medical indication. In particular, in one aspect, the invention provides for the use of a GLP-1 receptor agonist-containing composition as described herein in the manufacture of a medicament for the treatment of diabetes, especially type II diabetes, or for the medical or cosmetic treatment of excess bodyweight and/or obesity. In the case of medical treatment, the composition is typically administered to a subject in medical need thereof (e.g. having diabetes, excess bodyweight or obesity). In the case of cosmetic treatment, the subject may not have an identifiable medical need thereof, but may, for example, have a body mass index in the slightly overweight, higher normal, or normal range, wherein the benefit from weight loss is largely or solely cosmetic rather than medical.

In a still further aspect, the present invention provides a method for the treatment of a human or non-human mammalian subject comprising administering to said subject any of the non-aqueous pre-formulations described herein. Preferably, in such an aspect, the present invention provides a method for the treatment of a human or non-human mammalian subject in need thereof with a GLP-1 receptor agonist, said method comprising administering to said subject a GLP-1 receptor agonist-containing pre-formulation as described herein, preferably a non-aqueous pre-formulation comprising a low-viscosity mixture of;
a) at least one neutral diacyl lipid and/or a tocopherol;
b) at least one phospholipid;
c) at least one biocompatible, (preferably oxygen containing) organic solvent;
d) at least one GLP-1 receptor agonist; and
e) at least one lipid soluble acid;

Preferably, the method of treatment is a method for the treatment of at least one condition selected from diabetes, type I diabetes, type II diabetes, excess bodyweight and obesity. Alternatively the method may be a method of cosmetic treatment (e.g. to aid in the reduction of body weight) of a healthy subject (e.g. one having a normal BMI). Such a method of cosmetic treatment may exclude medical treatment, and thus be a method of cosmetic but not medical treatment.

The invention further provides a method of treatment comprising administration of a GLP-1 receptor agonist composition as described herein, especially in a subject in need thereof. The method of treatment is particularly for the treatment of diabetes, especially type II diabetes.

In a yet further aspect, the present invention provides the use of;
a) at least one neutral diacyl lipid and/or a tocopherol;
b) at least one phospholipid;
c) at least one biocompatible, (preferably oxygen containing) organic solvent;
d) at least one GLP-1 receptor agonist; and
e) at least one lipid soluble acid;
in the manufacture of a low viscosity pre-formulation medicament for use in the in vivo formation of a depot for treatment of type I diabetes, type II diabetes, excess bodyweight and/or obesity.

In a still further aspect, the invention provides for the use of at least one lipid soluble acid in increasing the use of a lipid soluble acid in the stabilisation of at least one peptide active agent (e.g. a GLP-1 receptor agonist) in a lipid-based composition, the lipid based composition comprising a low viscosity mixture of;

i) a non-polymeric slow-release matrix
ii) at least one biocompatible, (preferably oxygen containing) organic solvent;
iii) said at least one peptide active agent; and
iv) said at least one lipid soluble acid;

In a yet still further aspect, the invention provides a method of stabilising at least at least one peptide active agent (e.g. a GLP-1 receptor agonist) in a lipid-based composition, said method comprising formulating said at least one peptide active agent with at least one lipid soluble acid in a the lipid composition, as a low viscosity mixture of;

i) a non-polymeric slow-release matrix
ii) at least one biocompatible, (preferably oxygen containing) organic solvent;
iii) said at least one peptide active agent; and
iv) said at least one lipid soluble acid;

The preferred non-polymeric slow-release matrices are those indicated herein in respect of any aspect of the invention.

By "stabilising" is indicated an increase in solubility or dispensability of a component (especially an active agent) in the non-polymeric (e.g. lipid-based) matrix, or alternatively an increase in the stability of the composition, especially with regard to the physical and chemical stability of the dissolved or dispersed active agent. An increase in stability may thus be demonstrated by dissolution, dispersion or suspension of a greater amount of active agent in the presence of the lipid soluble acid than would be achieved by equilibration, such as by agitation for a prolonged period (e.g. 5 days at 25° C.), in the absence of lipid soluble acid. Equally, an increase in stability may be demonstrated by the chemical and/or physical stability of a peptide active agent in a matrix for a greater period than would be observed in the absence of a lipid soluble acid. This would preferably be tested under conditions of typical storage, such as 0-5° C., 25° C. and/or ambient temperature. This is further described herein below.

In all aspects of the present invention, the preferred non-polymeric slow-release matrix component i) is preferably a lipid-based or acyl-saccharide-based matrix, and in particular, "non-polymeric" is used to indicate that the matrix does not contain any significant quantity of poly-lactate, poly-glycolate or poly-glycolate-co-lactate polymer (e.g. no more than 1% by weight).

A preferred acyl-saccharide-based matrix is acylated sucrose, particularly sucrose acetate isobutyrate, including the fully-acylated sucrose ester having two acetate groups to six isobutyrate groups sold by the DURECT corporation of California, USA as "SABER". The matrix component may consist of at least 80% acyl-saccharides and will preferably consist essentially of such in this embodiment.

The most preferred non-polymeric slow-release matrix in all aspects of the invention is a lipid-based matrix, which is to say a matrix comprising at least 80% and preferably consisting essentially of lipid (i.e. amphiphilic) components.

In the aspects of the invention relating to lipid-based systems, the lipid matrix will preferably be components a) and b), as indicated herein. Components a) and b) will preferably be:

a) at least one diacyl glycerol and/or at least one tocopherol;
b) at least one phosphatidyl choline;

In all aspects, component c) will preferably be at least one oxygen containing organic solvent.

The pre-formulations of the present invention are highly advantageous in that they are stable to prolonged storage in their final "administration ready" form. As a result, they may readily be supplied for administration either by health professionals or by patients or their careers, who need not be fully trained health professionals and may not have the experience or skills to make up complex preparations. This is particularly important in long-duration, slow-effecting diseases such as diabetes.

In a yet further aspect, the present invention provides a disposable administration device (which is also to include a device component) pre-loaded with a measured dose of a non-aqueous pre-formulation of the present invention. Such a device will typically contain a single dose ready for administration, and will generally be sterile-packed such that the composition is stored within the device until administration. Suitable devices include cartridges, ampoules and particularly syringes and syringe barrels, either with integral needles or with standard (e.g. luer) fittings adapted to take a suitable disposable needle.

The pre-filled devices of the invention may also suitably be included in an administration kit, which kit also forms a further aspect of the invention. In a still further aspect, the invention thus provides a kit for the administration of at least one peptide active agent (e.g. at least one GLP-1 receptor agonist), said kit containing a measured dose of a formulation of the invention and optionally an administration device or component thereof. Preferably the dose will be held within the device or component, which will be suitable for i.m. or preferably s.c. administration. The kits may include additional administration components such as needles, swabs, etc. and will optionally and preferably contain instructions for administration. Such instructions will typically relate to administration by a route as described herein and/or for the treatment of a disease indicated herein above.

The invention provides for a pre-filled administration device as indicated herein and a kit as indicated herein comprising a non-aqueous pre-formulation as described herein.

In an alternative aspect of the present invention, the "kit" may contain at least two vessels, a first containing a low viscosity mixture of components i) and ii) (e.g. components a) to c)), as described here, and a second containing a measured dose of at least one peptide active agent (e.g. at least one GLP-1 receptor agonist) as described herein. The lipid soluble acid iv) (component e)) may be formulated with the active agent, or more preferably as part of the low viscosity mixture, which will then comprise components i), ii) and iv) (e.g. a) to c) and e)).

Such a "two component kit" may comprise the peptide active agent (e.g. GLP-1 analogue) as a powder formulation (optionally including component iv)) in one vial or pre-filled syringe and the matrix and solvent components of the formulation (i.e. components i), and ii, with or without iv), e.g. components a) to c) (and preferably e))) in a second vial or pre-filled syringe. In the case of two syringes, before injection, the pre-filled syringes are connected and the powder comprising active agent is mixed with the matrix formulation by moving the syringe barrels back and forth, forming a peptide solution or suspension which is injected. Alternatively, the liquid lipid formulation is drawn from one vial, or is pre-filled into a syringe, and is injected into a vial containing peptide powder. This formulation may subsequently be mixed by hand shaking or other suitable reconstitution method (e.g. vortex mixing etc.). The solvent component i) may be present in either or both vessels (e.g. vials or syringes). Where the solvent is at least partially constituted with the active agent, this will generally be in the form of a solution or suspension.

In this aspect, the invention therefore provides a two component kit comprising
i) a first vessel containing a low viscosity mixture of components i) and ii) (preferably a) to c)) as described herein;
ii) a second vessel containing at least one peptide active agent (preferably at least one GLP-1 receptor agonist),
iii) a lipid soluble acid optionally in a third vessel, preferably in the second vessel, or most preferably in the first vessel;
iv) optionally and preferably at least one of:
  1) at least one syringe (which may be one or both of said first and second vessels);
  2) a needle for administration, such as those described herein;
  3) instructions for generation of a composition of the invention from the contents of the first and second vessels;
  4) instructions for administration, whereby to form a depot as described herein.

Certain of the formulations of the present invention generate a non-lamellar liquid crystalline phase following administration. The use of non-lamellar phase structures (such as liquid crystalline phases) in the delivery of bioactive agents is now relatively well established. A most effective lipid depot system is described in WO2005/117830, and a highly preferred lipid matrix for use in the present invention is that described in that document, the full disclosure of which is hereby incorporated herein by reference. For a description of the most favourable phase structures of such formulations, attention is drawn to the discussion in WO2005/117830 and particularly to page 29 thereof.

As used herein, the term "low viscosity mixture" is used to indicate a mixture which may be readily administered to a subject and in particular readily administered by means of a standard syringe and needle arrangement. This may be indicated, for example by the ability to be dispensed from a 1 ml disposable syringe through a small gauge needle. Preferably, the low viscosity mixtures can be dispensed through a needle of 19 awg, preferably smaller than 19 gauge, more preferably 23 awg (or most preferably even 27 gauge) needle by manual pressure. In a particularly preferred embodiment, the low viscosity mixture should be a mixture capable of passing through a standard sterile filtration membrane such as a 0.22 μm syringe filter. A typical range of suitable viscosities would be, for example, 0.1 to 5000 mPas, preferably 1 to 1000 mPas at 20° C.

It has been observed that by the addition of small amounts of low viscosity solvent, as indicated herein, a very significant change in viscosity can be provided. For example, the addition of only 5% solvent to a lipid mixture can reduce viscosity 100-fold and addition of 10% may reduce the viscosity up to 10,000 fold. In order to achieve this non-linear, synergistic effect, in lowering viscosity it is important that a solvent of appropriately low viscosity and suitable polarity be employed. Such solvents include those described herein infra. Preferred low-viscosity mixtures include molecular solutions, including dispersions of the peptide active agent in a molecular solution of the other components.

In one preferred aspect, the present invention provides a pre-formulation comprising components a, b, c, e and at least one GLP-1 receptor agonist as indicated herein. The amounts of these components will typically be in the range 30-70% a), 30-60% b) and 0.1-20% c), with the GLP-1 receptor agonist present at 0.01% to 10%, (such as 40-70% a), 30-60% b) and 0.1-10% c), with the GLP-1 receptor agonist present at 0.1% to 10%).

Typically, component e) is present at a peptide active agent (e.g. GLP-t receptor agonist) to lipid soluble acid molar ratio of 1:1 to 1:30, preferably 1:1 to 1:20, and most preferably 1:1 to 1:15, e.g. 1:2 to 1:10. Since typical lipid soluble acid are of lower molecular weight than peptides such as the GLP-1 receptor agonist, the proportion by weight of lipid soluble acid may be relatively small. For example, with a small molecular weight pH adjuster (e.g. less than 500 amu), 0.1 to 5% of the composition may be lipid soluble acid, preferably 0.2 to 2%.

All % are specified by weight herein throughout, unless otherwise indicated. The formulations may consist of essentially only these components and in one aspect consist entirely of such components.

Preferable ranges for component a) are 33-60% (e.g. 43-60%), particularly 35-55% (e.g. 40-55%) and preferable ranges of component b) are 33-55% (e.g. 35-55%), particularly 35-50% (e.g. 40 to 50%).

Ratios of a:b are typically 40:60 to 70:30, preferably 45:55 to 60:40 and more preferably 48:52 to 55:45. Ratios of around 50:50 are highly effective.

The amount of solvent component ii) (e.g. component c)) in the non-aqueous pre-formulation will have a considerable effect upon several features. In particular, the viscosity and the rate (and duration) of release will alter significantly with the solvent level. The amount of solvent will thus be at least sufficient to provide a low viscosity mixture but will additionally be determined so as to provide the desired release rate. This may be determined by routine methods in view of the Examples below. Typically a level of 0.1 to 20%, particularly 0.1 to 15% solvent will provide suitable release and viscosity properties. This will preferably be 2 to 15% (e.g. 2 to 12%) and an amount of around 10% is highly effective.

One advantage of the compositions of the present invention over polymer formulations, such as PLGA spheres, is the low initial release ("non-burst profile") of active agent. This may be defined such that the area under a plasma concentration against time the curve during the first 24 hours is less than 15% of the area under the curve for the entire curve (measured or extrapolated from time 0 to infinity or from time 0 to the last sampling time point), more preferably less than 10% and most preferable less than 7%. This applies particularly to the acyl saccharide and lipid aspects of the invention and is discussed in more detail in WO 2005/117830.

As indicated above, the amount of component c in the pre-formulations of the invention will be at least sufficient to provide a low viscosity mixture (e.g. a molecular solution, see above) of components i) and ii) (a, b and c for the lipid aspect) and will be easily determined for any particular combination of components by standard methods.

Where a lipid matrix is used, the phase behaviour may be analysed by techniques such as visual observation in combination with polarized light microscopy, nuclear magnetic resonance, and cryo-transmission electron microscopy (cryo-TEM) to look for solutions, L2 or L3 phases, or liquid crystalline phases or as in the case of cryoTEM, dispersed fragments of such phases. Viscosity may be measured directly by standard means. As described above, an appropriate practical viscosity is that which can effectively be syringed and particularly sterile filtered. This will be assessed easily as indicated herein.

The preferred lipid-based matrix systems described herein comprise lipid components a) and b), plus solvent (c), active agent (d) and lipid-soluble acid (e) components. Component "a" as indicated herein is preferably at least one diacyl glycerol (DAG) and thus has two non-polar "tail" groups. The two non-polar groups may have the same or a differing number of carbon atoms and may each independently be saturated or unsaturated. Examples of non-polar groups include $C_6$-$C_{32}$ alkyl and alkenyl groups, which are typically present as the esters of long chain carboxylic acids. These are often described by reference to the number of carbon atoms and the number of unsaturations in the carbon chain. Thus, CX:Z indicates a hydrocarbon chain having X carbon atoms and Z unsaturations. Examples particularly include caproyl (C6:0), capryloyl (C8:0), capryl (C10:0), lauroyl (C12:0), myristoyl (C14:0), palmitoyl (C16:0), phytanoyl (C16:0), palmitoleoyl (C16:1), stearoyl (C18:0), oleoyl (C18:1), elaidoyl (C18:1), linoleoyl (C18:2), linolenoyl (C18:3), arachidonoyl (C20:4), behenoyl (C22:0) and lignoceroyl (C24:9) groups. Thus, typical non-polar chains are based on the fatty acids of natural ester lipids, including caproic, caprylic, capric, lauric, myristic, palmitic, phytanic, palmitolic, stearic, oleic, elaidic, linoleic, linolenic, arachidonic, behenic or lignoceric acids, or the corresponding alcohols. Preferable non-polar chains are palmitic, stearic, oleic and linoleic acids, particularly oleic acid.

Mixtures of any number of diacyl lipids may be used as component a. Preferably this component will include at least a portion of glycerol dioleate (GDO). A highly preferred example is DAG comprising at least 50%, preferably at least 80% and even comprising substantially 100% GDO.

Since GDO and other diacyl glycerols are products derived from natural sources, there is generally a certain proportion of "contaminant" lipid having other chain lengths etc. In one aspect, GDO as used herein is thus used to indicate any commercial grade of GDO with concomitant impurities (i.e. GDO of commercial purity). These impurities may be separated and removed by purification but providing the grade is consistent this is rarely necessary. If necessary, however, "GDO" may be essentially chemically pure GDO, such as at least 80% pure, preferably at least 85% pure and more preferably at least 90% pure GDO.

Component "b" in the preferred lipid matrices of the present invention is at least one phosphatidyl choline (PC). As with component a, this component comprises a polar head group and at least one non-polar tail group. The difference between components a and b lies principally in the polar group. The non-polar portions may thus suitably be derived from the fatty acids or corresponding alcohols considered above for component a. As with component a), the PC will contain two non-polar groups.

The phosphatidyl choline portion, even more suitably than any diacyl glycerol portion, may be derived from a natural source. Suitable sources of phospholipids include egg, heart (e.g. bovine), brain, liver (e.g. bovine) and plant sources including soybean. Such sources may provide one or more constituents of component b, which may comprise any mixture of phospholipids. Any single PC or mixture of PCs from these or other sources may be used, but mixtures comprising soy PC or egg PC are highly suitable. The PC component preferably contains at least 50% soy PC or egg PC, more preferably at least 75% soy PC or egg PC and most preferably essentially pure soy PC or egg PC.

In an alternative but equally preferred embodiment, the PC component may comprise synthetic dioleoyl PC. This is believed to provide increased stability and so will be particularly preferable for compositions needing to be stable to long term storage, and/or having a long release period in vivo. In this embodiment the PC component preferably contains at least 50% synthetic dioleoyl PC, more preferably at least 75% synthetic dioleoyl PC and most preferably essentially pure synthetic dioleoyl PC. Any remaining PC is preferably soy or egg PC as above.

Since the pre-formulations of the invention are to be administered to a subject for the controlled release of a peptide active agent, it is important that the components are biocompatible. In this regard, the preferred lipid matrices for use in the pre-formulations of the present invention are highly advantageous since both PC and DAGs are well tolerated and are broken down in vivo into components that are naturally present in the mammalian body.

A particularly favoured combination of components a and b are GDO with PC, especially GDO with soy PC. Appropriate amounts of each component suitable for the combination are those amounts indicated herein for the individual components in any combination. This applies also to any combinations of components indicated herein, where context allows.

Component iii) (including component c) as appropriate) of the pre-formulations of the invention is an organic solvent, preferably an oxygen containing organic solvent.

Since the pre-formulation is to generate a depot composition following administration (e.g. in vivo), typically upon contact with an aqueous fluid, it is desirable that this solvent be tolerable to the subject and be capable of mixing with the aqueous fluid, and/or diffusing or dissolving out of the pre-formulation into the aqueous fluid. Solvents having at least moderate water solubility are thus preferred.

In a preferred version, the solvent is such that a relatively small addition to the matrix composition (e.g. a mixture comprising a and b), i.e. preferably below 15%, gives large viscosity reductions, of one order of magnitude or more. As described herein, the addition of 10% solvent can give a reduction of two, or more orders of magnitude in viscosity over the solvent-free composition, or over a matrix containing an unsuitable solvent such as water, or glycerol.

Typical solvents suitable for use in the invention include at least one solvent selected from alcohols, ketones, esters (including lactones), ethers, amides and sulphoxides. Alcohols are particularly suitable and form the preferred class of solvents. Examples of suitable alcohols include ethanol, isopropanol, benzyl alcohol and glycerol formal. Ethanol is most preferred. Monools are preferred to diols and polyols. Where diols or polyols are used, this is preferably in combination with an at least equal amount of monool or other preferred solvent. Alternatively, diols such as propylene glycol may be used alone or more preferably with at least one fifth of the amount of mono-ol, especially ethanol (by weight). Examples of ketones include acetone, and propylene carbonate. Suitable ethers include diethylether, glycofurol, diethylene glycol monoethyl ether, dimethylisobarbide, and polyethylene glycols. Suitable esters include ethyl acetate, benzyl benzoate and isopropyl acetate and dimethyl sulphide is as suitable sulphide solvent. Suitable amides include n-methylpyrrolidone (NMP), 2-pyrrolidone and dimethylacetamide (DMA). Sulphoxides include methylsulphoxide and dimethylsulphoxide (DMSO).

A highly preferred combination for the lipid matrix aspect is soy PC, GDO and ethanol. As indicated above, appropriate amounts of each component suitable for the combination are those amounts indicated herein for the individual components, in any combination.

It is preferable that little or none of component c contains halogen substituted hydrocarbons since these tend to have lower biocompatibility. Where a portion of halogenated solvent such as dichloromethane or chloroform is necessary, this proportion will generally be minimised.

Component c as used herein may be a single solvent or a mixture of suitable solvents but will generally be of low viscosity. This is important because one of the key aspects of the present invention is that it provides pre-formulations that are of low viscosity and a primary role of a suitable solvent is to reduce this viscosity. This reduction will be a combination of the effect of the lower viscosity of the solvent and the effect of the molecular interactions between solvent and lipid composition. One observation of the present inventors is that the oxygen-containing solvents of low viscosity described herein have highly advantageous and unexpected molecular interactions with the lipid parts of the composition, thereby providing a non-linear reduction in viscosity with the addition of a small volume of solvent.

The viscosity of the "low viscosity" solvent component c (single solvent or mixture) should typically be no more than 18 mPas at 20° C. This is preferably no more than 15 mPas, more preferably no more than 10 mPas and most preferably no more than 7 mPas at 20° C.

The pre-formulations of the present invention typically do not contain significant amounts of water. Since it is essentially impossible to remove every trace of water from a lipid composition, this is to be taken as indicating that only such minimal trace of water exists as cannot readily be removed. Such an amount will generally be less than 1% by weight, preferably less that 0.5% by the weight of the pre-formulation. In one preferred aspect, the pre-formulations of the invention do not contain glycerol, ethylene glycol or propylene glycol and contain no more than a trace of water, as just described. The possible exception to this is when a larger amount of water is balanced by an appropriate amount of water-soluble organic solvent and is described above.

The pre-formulations of the present invention contain one or more peptide active agents. Such peptides may be naturally occurring or derived from natural peptides, or may be chemically modified or wholly synthetic peptide molecules. Any amino acids may be comprised in the peptides including those described herein, and the peptides may be chemically or enzymatically modified.

Typical peptide actives will be in the range of 500 to 100,000 amu in molecular weight and evidently include protein active agents. In one embodiment, the peptides can have at least one cationic charge at neutral and/or physiological pH, and most preferably will require at least one anionic counter-ion at pH 6.5 or above, preferably at pH 7.5 or above. This counter-ion will be physiologically acceptable, and may thus be a halide or the ion of a physiologically acceptable acid. Acetate counter ions are particularly preferred and therefore in one embodiment of the invention, the active agent is a peptide acetate. In an alternative embodiment, the peptide active agent may be essentially neutral, and may have an isoelectric point of between pH5 and pH8, preferably between pH5.2 and pH 7.5.

Examples of suitable classes of peptides include peptide hormones and synthetic analogues (such as luteinizing-hormone releasing hormone (LHRH) and analogues (eg, leuprorelin, goserelin, buserelin, tryptorelin, degarelix), incretins and incretin mimetics (such as GLP-1 & analogues or glucose-dependent insulinotropic peptide (GIP)), glucagon, insulin and analogues, interferons, vasopressins, calcitonins, etc.), cytokines, antibody fragments (FAbs; scVFs), antimicrobial peptides (g, corticostatins, defensins, histatins), specific targeting peptides (e.g., as the examples described in Current Opinion Genetics & Development 10, 71-77 (2006)), venom peptides (e.g., conopeptides), and immunogenic peptides (e.g., fragments of proteins used for vaccination purposes).

In one preferred embodiment of the present invention, the peptide active agent will not be a somatostatin, or any analogue or derivative thereof.

Most preferred active agents, which are used by way of example throughout the present specification are GLP-1 receptor agonists. Since GLP-1 is a peptide hormone, typical GLP-1 receptor agonists will be the native GLP-1 and its analogues. Generally, these will be peptides, especially of around 30 amino acids, e.g. 20 to 48, especially 25 to 45 (e.g. 25 to 38). Preferably such peptides will be structurally related to GLP-1, exendin-4 and/or one or more of the known analogues, including those listed here. Peptides may contain only amino acids selected from those 20 α-amino acids indicated in the genetic code, or more preferably may contain their isomers and other natural and non-natural amino acids, (generally α, β or γ, L- or D-amino acids) and their analogues and derivatives.

Preferred amino acids include those listed above as constituents of the known GLP-1 analogues.

Amino acid derivatives are especially useful at the termini of the peptides, where the terminal amino or carboxylate group may be substituted by or with any other functional group such as hydroxy, alkoxy, carboxy (on the N-terminal end), ester, amide, thio, amido, amino (on the C-terminal end), alkyl amino, di- or tri-alkyl amino, alkyl (by which is meant, herein throughout $C_1$-$C_{20}$ alkyl, preferably $C_1$-$C_{18}$ alkyl e.g. methyl; ethyl, n-propyl, isopropyl, n-butyl, iso-, sec- or t-butyl etc.), aryl (e.g phenyl, benzyl, napthyl etc), heteroaryl, or other functional groups, preferably with at least one heteroatom and preferably having no more than 20 atoms in total, more preferably no more than 10 and most preferably not more than 6 atoms (optionally excluding hydrogens).

By "GLP-1 receptor agonist", as used herein is indicated any peptide agonist of the GLP-1 receptor, including all modified and non-natural peptides such as those described herein, explicitly including those described herein in the background section. Preferably, these will be GLP-1 analogues or analogues of the naturally occurring agonist "exendin-4", including naturally occurring forms of GLP-1 and exendin-4, either human or from any other species. These analogues are peptides, peptide derivatives or peptide mimics. Peptide derived GLP-1 receptor agonists are most preferred, such as those indicated above and especially GLP-1(7-37), GLP-1(7-36) amide, Liraglutide, AVE-010 (ZP10), TH0318, BIM 51077, NN2211, CJC-1131, LY315902 and Exenatide (exendin-4). The specific sequences of several preferred GLP-1 receptor agonists are shown herein above, and these are all highly suitable. Additional suitable GLP-1 receptor agonists are also provided in the literature, and in particular these include the peptides and acyl peptides listed in *J Med Chem* 43, 1664-1669 (2000) (especially the GLP-1 analogues shown in table 1 on page 1665); the derivatives made possible by the work provided in *J. Med. Chem.* 47, 4128-4134 (2004), and in particular the structures conforming to the essential amino acids, sites derivatisable with fatty acids, and sites modifiable for improved peptidase resistance as summarised in FIG. 3 on page 4130; the known analogues and all analogues made available from the work described in *Diabetes Metab. Res. Rev.* 21, 313-331 (2005), including the analogues described on pages 322 to 323, plus analogues derivatised or formulated for peptidase resistance as described on pages 323 to 325; and all agonists described in *Curr. Med. Chem.*

10, 2471-2483 (2003), in particular those with sequences and modifications described on page 2477. These documents, and in particular the parts indicated form part of the disclosure of the present invention and are thus explicitly incorporated herein by reference.

In one typical embodiment, the peptide active agent (e.g. GLP-1 receptor agonist) will generally be formulated as 0.02 to 12% by weight of the total formulation. Typical values will be 0.1 to 10%, preferably 0.2 to 8% and more preferably 0.5 to 6%. These levels may be applied to all aspects of the invention, where context allows.

In a related embodiment, the peptide active agent (e.g. GLP-1 receptor agonist) will be formulated at a level which cannot easily be achieved in the absence of the lipid soluble acid component of the mixture. In such an embodiment, the peptide active agent (e.g. GLP-1 receptor agonist) content is typically at least 0.7%, preferably at least 1%, more preferably at least 2% by weight of formulation. Levels of at least 3% and at least 4% are achievable with the present invention, as are loading levels up to 8, 10 or 12%. Such compositions of the present invention typically not only contain a very high level of peptide active agent (especially GLP-1 receptor agonist), as indicated, but are additionally stable to storage without loss or degradation of the active agent for considerable periods, as indicated herein. Such periods will generally be at least a month at 25° C. or at 5° C., preferably at least 3 months, and more preferably at least 6 months at 5° C. or alternatively at 25° C. These degrees of stability are applicable to all aspects of the invention, where context allows.

In one embodiment, the compositions of the present invention rely upon the effect of the lipid soluble acid to allow for a loading of peptide active agent (e.g. GLP-1 receptor agonist) at a level above that which could be achieved in the absence of that component. Obviously, a high loading level is highly advantageous and is has been surprisingly established by the present inventors that by including the lipid soluble acids specified herein, in the amounts indicated, a much higher loading of peptide active agents (particularly GLP-1 receptor agonists) can be obtained (see examples). The level of peptide active agent (e.g. GLP-1 receptor agonist) which could be loaded in a composition is easily established by equilibration of the composition with excess active agent (e.g. by slow end-over-end rotation for 5 days at 25° C.—see Examples). The present compositions can and preferably do contain a greater amount of peptide active agent (particularly GLP-1 receptor agonist) than can be achieved by equilibration in the absence of the lipid soluble acid component. This can apply in all aspects of the present invention, where context allow.

Where the peptide active agent is a GLP-1 receptor agonist, suitable doses for inclusion in the formulation, and thus the volume of formulation used, will depend upon the release rate (as controlled, for example by the solvent type and amount used, the P80 content and so forth) and release duration, as well as the desired therapeutic level, the activity of the specific agent, and the rate of clearance of the particular active chosen. Typically an amount of around 0.05 to 40 mg per week of depot duration, preferably 0.1 to 20 mg per week duration for a duration of 1 to 24 weeks, preferably 2 to 16 (e.g. 8, 10 or 12) weeks. A total dose of 0.05 to 250 mg per dose would be suitable for providing a therapeutic level for between 7 and 168 days. This will preferably be 0.1 to 192 mg, e.g. 0.2 to 160 mg, 0.1 to 1.6 mg, 20 to 160 mg etc. Evidently, the stability of the active and linearity of the release rate will mean that the loading to duration may not be a linear relationship. A depot administered every 30 days might have, for example 0.2 to 20 mg or a 90 day depot have 60 to 120 mg of active agent, such as one of the GLP-1 receptor agonists indicated herein. Evidently also, the biological half-life of the specific active will be particularly important. The half-life of native human GLP-1 (GLP-1(7-37) and GLP-1(7-36)amide), which is one preferred active, is less than 5 minutes, and so for sustained release, a relatively large amount (e.g. towards the higher end of the range) will be needed. For an analogue such as exenatide, with a much longer half-life, the amount needed will evidently be lower. Appropriate levels for other actives will be established easily by those of skill in the art by reference to the known therapeutic level, the desired duration of action and the volume which is to be injected. A good base calculation would be to multiply a typical daily dose of the active agent by the number of day's duration of the depot. The formulation can then be tested for linearity of release and adjusted as appropriate.

It is a remarkable development of the present formulations that very short half-life peptide active agents, including native human GLP-1 (GLP-1(7-37) and GLP-1(7-36)amide) can be prepared and administered in a depot precursor of the present invention, and will provide controlled release over several days or even weeks. This is in spite of the remarkably short biological half-life of the active agent (e.g. less than 1 hour, preferably less than 15 minutes, e.g. less than 5 minutes). Such a high performance in delivery of a short half-life active is not otherwise known and no other lipid depot system capable of sustained release of native human GLP-1 has been reported. Thus, in one embodiment, the active agent has a half-life of less than 1 hour, e.g. less than 15 minutes (such as GLP-1(7-37)) and the preformulation forms a depot which provides sustained release for at least 7 days, preferably at least 14 days, more preferably at least 28 days.

The "lipid soluble acid" component "e)" as used herein is generally a low molecular weight compound which would form an acidic solution in an aqueous medium (i.e. in water). Although referred to as an "acid" herein, and acting as an acid in aqueous solutions, this component does not generally act as a typical acid in the pre-formulations of the invention, since these are non-aqueous. In a preferred embodiment, such a lipid soluble acid has a molecular weight of less than 500 amu, e.g. less than 300 amu and more preferably less than 200 amu. Organic and mineral acids form preferred lipid soluble acids, especially those having low molecular weight as indicated. The lipid soluble acids will generally be those having a pKa of lower than 5, preferably lower than 4.7 and most preferably lower than 4.5. The acids must also be suitable for dissolution at the required level in the chosen matrix system. As the matrices are generally hydrophobic or amphiphilic, suitable acids are referred to herein as "lipid soluble". The suitability of any acid in any particular matrix system will be established by one of ordinary skill by simple routine testing. Since the lipid soluble acids are to be administered as part of a parenteral drug-release system, biocompatibility in the relevant quantities is also necessary. Particularly preferred lipid soluble acids are selected from benzoic acid, citric acid, sulphonic acids (e.g. methane sulphonic acid, benzene sulphonic acid or toluene sulphonic acid) and hydrohalic acids (e.g. hydrochloric acid, hydrobromic acid or hydroiodic acid). Most preferred lipid soluble acids are benzoic acid, citric acid, methane sulphonic acid, benzene sulphonic acid, toluene sulphonic acid and HCl.

In one alternative embodiment of the invention, the lipid soluble acid is not a hydrohalic acid (e.g. not HCl, not HBr and/or not HI). In this embodiment it is preferred that the lipid soluble acid is benzoic acid, citric acid or a sulphonic acid.

The lipid soluble acids are referred to herein as "acids" and in one preferred aspect they are formulated as at least essentially consisting of the acid in free acid form. In an alternative aspect, however, the lipid soluble acid may be the salt of the corresponding acid as described herein, wherein the counter-ion is a physiologically acceptable ion such as an alkali-metal or alkaline earth metal cation, an ammonium ion or a substituted ammonium ion. A mixture of such ions is evidently also suitable. In one corresponding embodiment, the counter-ion is the cation of the peptide active agent, or a mixture of ions including the cation of the peptide active agent.

The function of the lipid soluble acids in the compositions of the present invention is not immediately evident. Since the compositions are essentially free of water, the aqueous hydrogen ion concentration, which is the normal basis of pH, does not directly apply, and the lipid soluble acids must have an additional effect in these systems. Without being bound by theory, it is believed that the ions of the lipid soluble acids serve to stabilise the dissolution of the peptide (e.g. GLP-1 receptor agonist) active agents, which are typically also formulated as salts (generally the acetate salt). It has, however, been observed by the present inventors that the free acid form of the lipid-soluble acids is significantly more effective in stabilising dissolution of high levels of active agent than the corresponding salt. This is thought to be the result of the lower lipid solubility of the ionic form, especially where the positive counter-ion is poorly lipid-soluble. As a result, it is preferred that the lipid soluble acids are used in their free-acid form, or where a poly-acid is used, that all acid groups are in the free-acid form. This may be the case in all embodiments of the invention, but applies particularly to GLP-1 receptor agonists. Where an acid salt is used, the counter-ion must evidently be biotolerable, but it is preferable that this is has an organic counter ion, such as an ammonium ion (e.g. $R_4N^+$ where the four R groups are each H or $C_1$ to $C_6$ organic (e.g. hydrocarbyl or heterocyclic) groups, which may joint to form rings, and preferably no more than three R groups are H). The lipid soluble acids preferably do not comprise metal ions, (e.g. alkali metal or alkaline earth metal ions), such as sodium, potassium, magnesium or calcium ions. Sodium ions of the lipid soluble acids (e.g. sodium citrate) are preferably not present in the formulations, and/or are not added thereto or formulated therewith. Again, this may be the case in all embodiments of the invention, but applies particularly to GLP-1 receptor agonists.

In all aspects of the invention, the lipid soluble acid (component iv)/e)) is typically present at a molar ratio of peptide active agent to lipid soluble acid of 1:1 to 1:30, preferably 1:1 to 1:20, e.g. 1:1 to 1:15 and most preferably 1:2 to 1:10. Since typical lipid soluble acid are of lower molecular weight that the peptide active agent, the proportion by weight of lipid soluble acid may be relatively small. For example, with a small molecular weight pH adjuster (e.g. less than 500 amu), 0.1 to 5% of the composition may be lipid soluble acid, preferably 0.2 to 2%.

A sugar component may be present in the compositions of the present invention; and this may also serve to increase the loading and stability of the active agent. Preferred sugar components include lactose, and more preferably sucrose or trehalose. Where present, the sugar component may be present at 0.1 to 20%, preferably 0.5 to 10% by weight, more preferably 1 to 5% by weight.

Alternatively, there may be no sugar component present, for example, there may be no sucrose, no lactose, and/or no trehalose present in the composition. These may also be present at a low level, such that the sugars (e.g. sucrose, lactose, and/or trehalose) may each independently be present at 0 to 1%, preferably 0 to 0.5%.

Where the lipid soluble acid is citric acid or a citrate salt, the stabilisation of GLP-1 is very effective. In one embodiment, citric acid allows compositions of GLP-1 in the absence of any sugar component. Thus, where GLP-1 and citrate are used, it can be that there is no sugar component present, and in particular no sucrose, lactose or trehalose present. Alternatively, where present, the sugar component is at less than 1 wt %, preferably less than 0.5 wt %.

In an alternative embodiment, there may be a sugar (such as sucrose, lactose or preferably trehalose), present in the composition and in particular may be present at greater than 1%, for example at 1.5 to 5%. In such compositions, it is preferred that where the peptide active agent is a GLP-1 receptor agonist (especially a human GLP-1), the level of peptide active agent will be greater than 2% by weight, preferably greater than 2.5% by weight, e.g. at least 3% by weight. Suitable ranges include 2 to 15% by weight, e.g. 2.5 to 12% by weight, or 3 to 10% by weight of the total composition. Thus, where citrate, GLP-1 and a sugar, such as sucrose, lactose and/ore trehalose, (at a level of at least 1%, e.g. 1-3%) are present in the formulation, the GLP-1 will preferably be formulated at greater than 2% by weight.

In one particularly preferred embodiment of the present invention, the compositions (preformulations and resulting depots) may include at least one biocompatible polyethyleneoxide or poly(ethylene glycol) (PEG) fragmentation agent, such as a PEG grafted lipid and/or surfactant. These agents are useful in all compositions, and are believed to increase the stability of the peptide active agent (e.g. GLP-1 receptor agonist), even at low concentrations. In a particularly advantageous embodiment, however, they may be highly useful for providing lipid depots with shorter duration (e.g. 5 to 30 days, especially 7 to 21 days). This is because such a component will tend to fragment the depot into smaller pieces in situ and thus the degradation of the depot will not only be biodegradation but also "physical" erosion, thus enabling faster release (but still without any significant burst). These are most preferable with the lipid matrices described herein.

If included in the lipid-based pre-formulation, the content of such a fragmentation agent component, would be 0.1-30%, more preferably 0.5-25% and most preferably 2-20%. In particular, 0.1 to 1% (preferably 0.2 to 0.7%) is particularly useful for stabilising the active agent, such as GLP-1 receptor agonist, and 1 to 25%, preferably 5 to 20% is beneficial in controlling the depot release period. Mother advantage of including a fragmentation agent is that it may be beneficial from a chronic use point of view. Users of GLP-1 receptor agonist depot products, as well as users of many other peptide depot products are typically long-term users, and such a depot erodes faster and thus the depot will vanish quicker from the injection site, allowing earlier re-use of the site and causing a lesser build-up of connective tissue around the sites of injection. Furthermore, the inclusion of such an agent may even improve the already good biotolerability/biocompatibility.

The most preferred fragmentation agent is Polysorbate 80 (P80). Other useful agents include other Polysorbates (e.g. Polysorbate 20), PEGylated phospholipids (PEG-lipids such as DSPE-PEG(2000), DSPE-PEG(5000), DOPE-PEG (2000) and DOPE-PEG(5000)), Solutol HS 15, PEGylated fatty acids (e.g. PEG-oleate), block co-polymers such as Pluronic® F127 and Pluronic® F68, ethoxylated castor oil derivatives (e.g. Chremophores), PEGylated glyceryl fatty acid esters (such as TMGO-15 from Nikko Chemicals) and PEGylated tocopherols (such as d-alpha tocopheryl poly (ethylene glycol) 1000 succinate known as Vitamin E TPGS from Eastman.

The peptide active (e.g. GLP-1 receptor agonist) as a powder (e.g. in the kit of the invention), as well as active agent dissolved in the lipid formulation, may gain stability (both storage and in vivo stability) by certain stabilising additives. Such additives include sugars (e.g. sucrose, trehalose, lactose etc.), polymers (e.g. polyols such as carboxy methyl cellulose), small amounts of surface active agents (e.g. P80—see above), antioxidants (such as ascorbic acid, EDTA and citric acid), amino acids (such as methionine, glutamate, lysine etc.) and anionic lipids and surface active agents (such as dioleoyl phosphatidyl glycerol (DOPG), palmitoyloleoyl phosphatidylglycerol (POPG) and oleic acid (OA)).

One preferred additive agent is a thiol-based antioxidant. Like essentially all organic molecules, lipids and biologically active agents are thermodynamically unstable to oxidation. As a result, many lipid formulations, including those comprising bioactive agents such as APIs are susceptible to degradation upon storage, especially by oxidation.

Unfortunately, many common antioxidants are not highly compatible with lipid systems. Indeed, the present inventors have surprisingly established that some antioxidants commonly used in previous systems can cause increased degradation of active agents in a lipid system. This applies particularly to peptide active agents. The present inventors have therefore analysed a variety of potential antioxidant compounds and classes for use with lipid based matrix systems and have surprisingly found that one particularly class of antioxidants is unusually well suited for use in these systems.

The present inventors have now established that thiolated antioxidants, particularly mono-thioglycerol (MTG), cysteine, and cysteine analogues such as N-acetyl cysteine, are highly effective in lipid based systems, especially in combination with the lipid soluble acids as indicated herein. Thus in a preferred embodiment of the present invention; an antioxidant component is included comprising a thiolated antioxidant, preferably thiolated sugar, thiolated amino acid, a thiolated amino ester, or a thiolated polyol. Mono-thioglycerol, N-acetyl cysteine or cysteine are preferred thiolated antioxidants.

The antioxidant component is generally included in the range 0.01 to 2.0% by weight of the total pre-formulation. This is most preferably 0.05 to 1.0%, and around 0.2 to 0.5% of antioxidant (particularly MTG) is particularly preferred, especially in combination with the other preferred components and ranges indicated herein above and below.

The reason for the utility of thiolated antioxidants in general and MTG in particular is not known. Without being bound by theory, it is believed that MTG acts as an effective chain-breaking donating antioxidant according to established mechanisms whereby peroxyl radicals (ROO.) are neutralized. Their quenching by the thiolated antioxidant breaks the cycle of further oxidative degradation. Thiols such as MTG and N-acetyl cysteine may also regenerate certain components from their oxidized forms.

Stability data using a number of different antioxidants demonstrate that thiolated antioxidants are surprisingly more efficient than other antioxidants in suppressing the oxidative degradation of bioactive agents. Thiolated antioxidants can also show a synergistic effect in combination with the lipid soluble acids of the present invention, in maintaining the chemical and physical stability of the peptide active agent and complete pre-formulation.

The pre-formulations of the present invention are generally formulated to be administered parenterally. This administration will generally not be an intra-vascular method but will preferably be subcutaneous (s.c.), intracavitary or intramuscular (i.m.). Typically the administration will be by injection, which term is used herein to indicate any method in which the formulation is passed through the skin, such as by needle, catheter or needle-less (needle-free) injector. It is, however, possible to take advantage of the high loading and other beneficial characteristics of the present formulation in non-parenteral applications, including topical or systemic application to skin, mucous membranes, nasal, buccal and/or oral cavities. Preferably, such non-parenteral administration is for topical use.

Preferred parenteral administration is by i.m or s.c. injection, most preferably by deep s.c. injection. An important feature of the composition of the invention is that it can be administered both by i.m. and s.c. and other routes without toxicity or significant local effects. It is also suitable for intracavital administration. The deep s.c. injection has the advantage of being less deep and less painful to the subject than the (deep) i.m. injection used for some current depots and is technically most suitable in the present case as it combines ease of injection with low risk of local side effects. It is a surprising observation of the present inventors that the formulations provide sustained release of active agent over a predictable time period by both subcutaneous and intramuscular injection. This therefore allows the site of injection to be varied widely and allows the dose to be administered without detailed consideration of the tissue depth at the site of injection.

The preferred lipid matrix-based pre-formulations of the present invention provide non-lamellar liquid crystalline depot compositions upon exposure to aqueous fluids, especially in vivo. As used herein, the term "non-lamellar" is used to indicate a normal or reversed liquid crystalline phase (such as a cubic or hexagonal phase) or the L3 phase or any combination thereof. The term liquid crystalline indicates all hexagonal, all cubic liquid crystalline phases and/or all mixtures thereof. Hexagonal as used herein indicates "normal" or "reversed" hexagonal (preferably reversed) and "cubic" indicates any cubic liquid crystalline phase unless specified otherwise. The skilled reader will have no difficulty in identifying those compositions having appropriate phase behaviour by reference to the description and Examples provided herein, and to WO2005/117830, but the most favoured compositional area for phase behaviour is where ratio of components a:b are in the region of equality (e.g. around 35:65 to 65:35, preferably 42:58 to 58:42, most preferably 46:54 to 54:46).

It is important to appreciate that the pre-formulations of the present invention are of low viscosity. As a result, these pre-formulations must not be in any bulk liquid crystalline phase since all liquid crystalline phases have a viscosity significantly higher than could be administered by syringe or spray dispenser. The pre-formulations of the present invention will thus be in a non-liquid crystalline state, such as a solution, $L_2$ or $L_3$ phase, particularly solution or $L_2$. The $L_2$ phase as used herein throughout is preferably a "swollen" $L_2$ phase containing greater than 10 wt % of solvent (component c) having a viscosity reducing effect. This is in contrast to a "concentrated" or "unswollen" $L_2$ phase containing no solvent, or a lesser amount of solvent, or containing a solvent (or mixture) which does not provide the decrease in viscosity associated with the oxygen-containing, low viscosity solvents specified herein.

Upon administration, the preferred lipid-based pre-formulations of the present invention undergo a phase structure transition from a low viscosity mixture to a high viscosity (generally tissue adherent) depot composition. Generally this will be a transition from a molecular mixture, swollen $L_2$ and/or $L_3$ phase to one or more (high viscosity) liquid crystalline phases such as normal or reversed hexagonal or cubic liquid crystalline phases or mixtures thereof. Further phase transitions may also take place following administration. Obviously, complete phase transition is not necessary for the functioning of the invention but at least a surface layer of the administered mixture will form a liquid crystalline structure. Generally this transition will be rapid for at least the surface region of the administered formulation (that part in direct contact with air, body surfaces and/or body fluids). This will most preferably be over a few seconds or minutes (e.g. from 1 second up to 30 minutes, preferably up to 10 minutes, more preferably 5 minutes of less). The remainder of the composition may change phase to a liquid crystalline phase more slowly by diffusion and/or as the surface region disperses.

Without being bound by theory, it is believed that upon exposure (e.g. to body fluids), the pre-formulations of the invention lose some or all of the organic solvent included therein (e.g. by diffusion) and take in aqueous fluid from the bodily environment (e.g. the in vivo environment). In the case of an acyl-saccharide matrix, this with cause a rapid increase in viscosity as solvent is lost, and in the case of a lipid matrix, at least a part of the formulation preferably generates a non-lamellar, particularly liquid crystalline phase structure. In most cases these non-lamellar structures are highly viscous and are not easily dissolved or dispersed into the in vivo environment. The result is a monolithic "depot" generated in vivo with only a limited area of exposure to body fluids. Furthermore, because the non-lamellar structure has large polar, apolar and boundary regions, the lipid depot is highly effective in solubilising and stabilising active agents such as peptides and protecting these from degradation mechanisms. As the depot composition formed from the pre-formulation gradually degrades over a period of days, weeks or months, the active agent is gradually released and/or diffuses out from the composition. Since the environment within the depot composition is relatively protected, the pre-formulations of the invention are highly suitable for active agents with a relatively low biological half-life (see above).

The depot systems formed by the formulations of the present invention are highly effective in protecting the active agent from degradation and thus allow an extended release period. Comparative tests have been carried out between the known PLGA slow-release product and preferred formulations of the present invention containing GDO, soy PC, ethanol and active agents. These indicate that formulations of the present invention give lesser degradation under simulated in vivo conditions than known compositions. The formulations of the invention thus may provide in vivo depots of GLP-1 receptor agonists which require administration only once every 7 to 360 days (e.g. 20 to 360 days), preferably 30 to 240 days (e.g. 30 to 168 days), more preferably 60 to 180 days (e.g. around 90 days, such as 60 to 120 or 90±7 days). Alternatively, in a further preferred embodiment, the durations are somewhat shorter, preferably 10 to 240 days (e.g. 20 to 168 days), more preferably 14 to 180 days (e.g. around 60 days, such as 6 to 10 weeks). Evidently, a longer stable release period is desirable for patient comfort and compliance, as well as demanding less time from health professionals if the composition is not to be self-administered. Where the composition is to be self-administered, patient compliance may be aided by a weekly (e.g. every 7 days, optionally ±1 day) or monthly (e.g. every 28 or 30 days (optionally ±7 days)) administration so that the need to administer is not forgotten.

A considerable advantage of the depot precursors of the present invention is that they are stable homogeneous phases. That is to say, they may be stored for considerable periods (preferably at least 6 months) at room or refrigerator temperature, without phase separation. As well as providing advantageous storage and facile administration, this allows for the dose of GLP-1 receptor agonist to be selected by reference to the species, age, sex, weight, and/or physical condition of the individual subject, by means of injecting a selected volume.

The present invention thus provides for methods comprising the selection of a dosing amount specific to an individual, particularly by subject weight. The means for this dose selection is the choice of administration volume.

In combination with the features and preferred features indicated herein, the pre-formulations of the invention may have one or more of the following preferred features independently or in combination:

All proportions indicated herein may optionally be varied by up to 10% of the amount specified, optionally and preferably by up to 5%;

Component a) comprises, consists essentially of or preferably consists of GDO;

Component b) comprises, consists essentially of or preferably consists of soy PC;

Component c) comprises, consists essentially of or preferably consists of a 1, 2, 3 or 4 carbon alcohol, preferably isopropanol or more preferably ethanol;

Component e) comprises, consists essentially of or preferably consists of a sulphonic acid or hydrohalic acid, preferably methane sulfonic acid (MeSulf), benzene sulfonic acid (BzSulf), toluene sulphonic acid (TSulf), benzoic acid, citric acid or anhydrous hydrogen chloride;

The pre-formulation contains at least one GLP-1 receptor agonist selected from those described or referred to herein, preferably GLP-1(7-37), GLP-1(7-36)amide, Liraglutide, AVE-010, TH-0318, LY548806 or exenatide;

The pre-formulation has a low viscosity as indicated herein.

The pre-formulation comprises a lipid matrix and forms a liquid crystalline phase as indicated herein upon in vivo administration.

The pre-formulation generates a depot following in vivo administration, which depot releases at least one GLP-1 receptor agonist at a therapeutic level over a period of at least 7 days, preferably at least 21 days, more preferably at least 30 days.

The pre-formulation has a higher loading of peptide active agent (e.g. GLP-1 receptor agonist) than is stable in the same formulation in the absence of the pH adjusting (lipid soluble acid) component e).

The pre-formulation has a higher loading of peptide active agent (e.g. GLP-1 receptor agonist) than is obtainable by equilibration at 25° C. of the same formulation in the absence of the pH adjusting component e).

In combination with the features and preferred features indicated herein, the method(s) of treatment of the present invention may have one or more of the following preferred features independently or in combination:

The method comprises the administration of at least one formulation with one or more preferred features as indicated above;

The method comprises the administration of at least one formulation as indicated herein by i.m., s.c. or preferably deep s.c. injection;

The method comprises administration by means of a pre-filled administration device as indicated herein;

The method comprises administration through a needle no larger than 20 gauge, preferably smaller than 20 gauge, and most preferably 23 gauge or smaller;

The method comprises a single administration every 7 to 360 days, preferably 7 to 120 days, more preferably 14 to 60 days.

The method comprises a single administration every 14 to 180 days, preferably around 60 days.

In combination with the features and preferred features indicated herein, the use(s) of the pre-formulations indicated herein in the manufacture of medicaments may have one or more of the following preferred features independently or in combination:

The use comprises the use of at least one formulation with one or more preferred features as indicated above;

The use comprises the manufacture of a medicament for administration of at least one formulation as indicated herein by i.m., s.c. or preferably deep s.c. injection;

The use comprises the manufacture of a medicament for administration by means of a pre-filled administration device as indicated herein;

The use comprises the manufacture of a medicament for administration through a needle no larger than 20 gauge, preferably smaller than 20 gauge, and most preferably 23 gauge or smaller;

The use comprises the manufacture of a medicament for administration once every 7 to 360 days, preferably 7 to 120 days, more preferably 14 to 60 days.

In combination with the features and preferred features indicated herein, the pre-filled devices of the invention may have one or more of the following preferred features independently or in combination:

They contain a preferred formulation as indicated herein;

They comprise a needle smaller than 20 gauge, preferably no larger than 23 gauge;

They contain a single dose of 0.05 to 250 mg of GLP-1 receptor agonist, preferably 0.1 to 100 mg and more preferably 1-50 mg;

They contain GLP-1(7-37), GLP-1(7-36)amide, TH-0318, Liraglutide, exenatide or AVE-010, at around 0.05 to 250 mg;

They contain a homogeneous mixture of a composition of the invention in ready-to-inject form.

They contain a formulation of components a) to c) for combination with a GLP-1 receptor agonist whereby to form a preformulation of the invention.

They contain a GLP-1 receptor agonist for combination with a formulation of components a) to c), whereby to form a preformulation of the invention.

They contain a total volume for administration of no more than 5 ml, preferably no more than 3 ml more preferably no more than 2 ml.

In combination with the features and preferred features indicated herein, the kits of the invention may have one or more of the following preferred features independently or in combination:

They contain a preferred formulation as indicated herein;

They contain a pre-filled device as indicated herein;

They contain a needle smaller than 20 gauge, preferably no larger than 23 gauge;

They contain a single dose of 0.05 to 250 mg of GLP-1 receptor agonist, preferably 0.1 to 100 mg and more preferably 1-50 mg;

They contain GLP-1(7-37), GLP-1(7-36)amide, TH-0318, Liraglutide or AVE-010, at around 0.05 to 250 mg;

They contain a "two compartment kit" comprising at least two vessels containing a lipid formulation of the invention and a GLP-1 receptor agonist powder, respectively.

They contain a total volume for administration of no more than 5 ml, preferably no more than 3 ml more preferably no more than 2 ml.

They contain instructions for administration by a route and/or at a frequency as indicated herein;

They contain instructions for administration for use in a method of treatment as described herein.

The Invention will now be further illustrated by reference to the following non-limiting Examples and the attached Figures, in which;

FIG. 1 shows the viscosity reducing effect on addition of solvents.

FIG. 2 displays stability data supporting the highly favourable storage stability obtained with formulation compositions of the invention.

FIG. 3 shows the level of breakdown products in a composition of the invention stored for four weeks at 5° C.

EXAMPLES

Example 1: Availability of Various Liquid Crystalline Phases in the Depot by Choice of Composition Injectable formulations containing different proportions of phosphatidyl choline (PC) ("SPC"—Lipoid S100) and glycerol dioleate (GDO) and with ethanol (EtOH) as solvent were prepared to illustrate that various liquid crystalline phases can be accessed after equilibrating the depot precursor formulation with excess water.

Appropriate amounts of PC, GDO and EtOH were weighed in glass vials and the mixture was placed on a shaker until the PC completely dissolved to form a clear liquid solution. GDO was then added to form an injectable homogenous solution.

Each formulation was injected in a vial and equilibrated with excess water. The phase behaviour was evaluated visually and between crossed polarizes at 25° C. Results are presented in Table 1.

TABLE 1

| Formulation | PC (wt %) | GDO (wt %) | EtOH (wt %) | Phase in $H_2O$ |
| --- | --- | --- | --- | --- |
| A | 22.5 | 67.5 | 10.0 | $L_2$ |
| B | 28.8 | 61.2 | 10.0 | $I_2$ |
| C | 45.0 | 45.0 | 10.0 | $I_2/H_{II}$ |
| D | 63.0 | 27.0 | 10.0 | $H_{II}/L_\alpha$ |

$L_2$ = reversed micellar phase
$I_2$ = reversed cubic liquid crystalline phase
$H_{II}$ = reversed hexagonal liquid crystalline phase
$L_\alpha$ = lamellar phase

Example 2

Viscosity in PC/GDO (5:5) or PC/GDO (4:6) on Addition of Solvent (EtOH, PG and NMP)

A mixture of PC/GDO/EtOH with approximately 25% EtOH was manufactured according to the method in Example 1. All, or nearly all, of the EtOH was removed from the mixture with a rotary evaporator (vacuum, 40° C. for 1 h followed by 50° C. for 2 h) and the resulting mixture was weighed in a glass vial after which 1, 3, 5, 10 or 20% of a solvent (EtOH, propylene glycol (PG) or n-methylpyrrolidone (NMP)) was added. The samples were allowed to equilibrate several days before the viscosity was measured with a CarriMed CSL 100 rheometer equipped with automatic gap setting.

This example clearly illustrates the need for solvent with certain depot precursors in order to obtain an injectable formulation (see FIG. 1). The viscosity of solvent-free PC/GDO mixtures increases with increasing ratio of PC. Systems with low PC/GDO ratio (more GDO) are injectable with a lower concentration of solvent.

Example 3: Degradation of Depot Formulation in the Rat

Various volumes (1, 2, 6 ml/kg) of the depot precursor (36% wt PC, 54% wt GDO, and 10% wt EtOH) were injected in the rat and were removed again after a period of 14 days. It was found that substantial amounts of the formulations were still present subcutaneously in the rat after this time, see Table 3.

TABLE 3

| Dose (ml/kg) | Mean diameter day 3 (mm) | Mean diameter day 14 (mm) |
|---|---|---|
| 1 (n = 3) | 15.8 | 12.5 |
| 2 (n = 3) | 18.5 | 15.3 |
| 6 (n = 3) | 23.3 | 19.3 |

Example 4: Preparation of a GLP-1 Formulation without pH-Adjusting Agent

The GLP-1 substance and the excipients used in example 4 to 8 are presented in the Table below.

GLP-1 Substance and Excipients Used in the Examples 4 to 8:

| Name | Abbreviation | Supplier |
|---|---|---|
| GLP-1(7-36)amide, acetate salt | GLP-1(Ac) | PolyPeptide Laboratories, Inc., CA, USA |
| Phosphatidylcholine, soy | SPC | Lipoid, Germany |
| Glycerol dioleate | GDO | Danisco, Denmark |
| Ethanol (99.5%) | EtOH | Kemetyl, Sweden |
| Propylene glycol | PG | Apoteket, Sweden |

A lipid formulation comprising 1.08 g SPC, 1.08 g GDO, 0.08 g EtOH and 0.26 g PG was mixed in a 5 mL glass vial (composition: SPC/GDO/EtOH/PG=43.2/43.2/3.2/10.4 wt %). The vial was placed on a mixing table (end-over-end mixing) for approximately 2 hours at RT. A transparent and homogenous formulation was obtained.

0.02 g of GLP-1(Ac) was weighed into a 2 mL glass vial and 1.98 g of the lipid formulation, prepared as above, was added (giving a total GLP-1(Ac) load of 1 wt %). The formulation was mixed on a vortex mixer (to disperse the GLP-1(Ac) powder in the formulation) and then placed on a mixing table at room temperature for constant end-over-end mixing. After 5 days the sample still contained a lot of undissolved GLP-1(Ac) as assessed visually and the sample was therefore centrifuged at 5000 rpm for 15 minutes to obtain a clear supernatant.

The GLP-1 concentration in the supernatant was assayed by a normal phase (NP) HPLC method using UV detection.

The assayed GLP-1 (equivalents base—GLP-1(0)) concentration in the sample was 6.25 mg/g (0.625 wt %). Because of the long equilibration time used (5 days) this value is taken as the maximum GLP-1 concentration achievable in the lipid formulation without the addition of pH-adjusting agent.

Example 5: Preparation of GLP-1 Formulations with Methane Sulfonic Acid (MeSulf) as pH-Adjusting Agent A lipid formulation comprising SPC, GDO, EtOH, PG and MeSulf (Sigma-Aldrich, Sweden) was prepared as described in Example 4. The lipid composition was the following: SPC/GDO/EtOH/PG/MeSulf=43.2/43.2/3.0/10.0/0.5 wt %.

The required amount of GLP-1(Ac) powder was weighed into 2 mL glass vials followed by addition of the lipid formulation in an amount appropriate for achieving nominal drug loads of approximately 3 to 6 wt % GLP-1(0). The samples were briefly vortexed followed by continuous end-over-end rotation at room temperature until completely homogenous and transparent samples were obtained (1-3 days).

The concentration of GLP-1 (expressed as equivalents GLP-1 base=GLP-1(0)) in the respective formulations as determined by HPLC is given in the Table below.

GLP-1 Drug Load in Lipid Formulations Containing MeSulf

| Formulation | Nominal GLP-1(0) conc./wt % | Assayed (HPLC) GLP-1(0) conc./wt % | Excess GLP-1 load compared with Example 4* |
|---|---|---|---|
| A | 3.00 | 3.07 | 4.91 |
| B | 3.73 | 3.77 | 6.03 |
| C | 4.61 | 4.58 | 7.33 |
| D | 5.43 | 5.36 | 8.54 |

*Calculated as the ratio between the assayed GLP-1(0) concentration with MeSulf as pH-adjusting agent and the concentration found in the formulation without MeSulf (Example 4)

Example 6: Preparation of GLP-1 Formulation with Anhydrous Hydrogen Chloride (HCl) as pH-Adjusting Agent A lipid formulation comprising SPC, GDO, PG and EtOH.HCl (1.25M HCl in EtOH from Fluka, Sweden) was prepared as described in Example 4. The lipid composition was the following: SPC/GDO/PG/EtOH.HCl=43.0/43.0/10.0/4.0 wt %.

The required amount of GLP-1(Ac) powder was weighed into a 2 mL glass vial followed by addition of the lipid formulation. The sample was briefly vortexed followed by continuous end-over-end rotation at room temperature until a completely homogenous and transparent sample was obtained (1 day).

The concentration of GLP-1 (expressed as GLP-1 base=GLP-1(0)) in the formulation as determined by HPLC is given in the Table below.

GLP-1 Drug Load in Lipid Formulations Containing HCl

| Formulation | Nominal GLP-1(0) conc./wt % | Assayed (HPLC) GLP-1(0) conc./wt % | Excess GLP-1 load compared with Example 4* |
|---|---|---|---|
| E | 3.68 | 3.66 | 5.86 |

*Calculated as the ratio between the assayed GLP-1(0) concentration with HCl as pH-adjusting agent and the concentration found in the formulation without HCl (Example 4)

Example 7: Preparation of GLP-1 Formulations Containing Polysorbate 80 (P80) and with Methane Sulfonic Acid (MeSulf) as pH-Adjusting Agent A lipid formulation comprising SPC, GDO, P80 (Croda, USA), EtOH, PG and MeSulf was prepared as described in Example 4. The lipid composition was the following: SPC/GDO/P80/EtOH/PG/MeSulf=41.0/41.0/5.0/3.0/10.0/0.5 wt %.

The required amount of GLP-1(Ac) powder was weighed into 2 mL glass vials followed by addition of the lipid formulation in an amount appropriate for achieving nominal drug loads of 3, 4, 5 and 6 wt % GLP-1(0). The samples were briefly vortexed followed by continuous end-over-end rotation at room temperature until completely homogenous and transparent samples were obtained (1-3 days) indicating complete dissolution of GLP-1 in the lipid formulation.

Example 8: Stability of GLP-1 in Formulations Containing MeSulf as pH-Adjusting Agent Lipid formulations containing MeSulf were prepared as described in Example 4.

The required amount of GLP-1(Ac) powder was weighed into 6 mL glass vials followed by addition of the lipid formulation in an amount appropriate for achieving nominal drug loads of 3 wt % GLP-1(0). The samples were briefly vortexed followed by continuous end-over-end rotation at RT until completely homogenous and transparent samples were obtained (1-3 days). The nominal composition of the samples is given in the Table below.

Nominal Composition (Wt %) of Formulations for Stability Study

| Formulation | GLP-1(0)* | SPC | DOPC** | GDO | PG | EtOH | MeSulf |
|---|---|---|---|---|---|---|---|
| F | 3.0 | 41.7 | — | 41.7 | 10.0 | 3.0 | 0.5 |
| G | 3.0 | — | 41.7 | 41.7 | 10.0 | 3.0 | 0.5 |

*equivalents GLP-1 free base (GLP-1(0)).
**Synthetic Dioleoyl Phosphatidylcholine (DOPC) from Lipoid, Germany.

The samples were filled in 1 mL glass vials, capped with Teflon-coated rubber stoppers and stored at 5° C. in a Termak climate chamber. After 4 weeks, the samples were taken out for analysis of GLP-1 content, ID and degradation products using a normal phase HPLC assay and UV detection (214 nm). The results displayed in FIGS. 2 and 3 reveal highly favourable storage stability of the formulations with essentially no degradation (within the error limits of the assay) of GLP-1 during the investigated time period.

The invention claimed is:

1. A non-aqueous pre-formulation comprising a low viscosity mixture of:
   a) 30-70 wt. % of at least one neutral diacyl lipid and/or tocopherol;
   b) 30-60 wt. % of at least one phospholipid;
   c) at least one biocompatible, organic solvent comprising ethanol;
   d) at least one peptide active agent other than a GLP-1 receptor agonist; and
   e) 0.1-5% wt. % of at least one lipid soluble acid selected from methane sulfonic acid or hydrochloric acid;
   wherein the molar ratio of said peptide active agent to said lipid soluble acid is 1:1 to 1:30;
   wherein the pre-formulation forms, or is capable of forming, at least one liquid crystalline phase structure upon contact with an aqueous fluid.

2. A non-aqueous pre-formulation as claimed in claim 1 wherein component a) comprises at least one diacyl glycerol; and component b) comprises at least one phosphatidyl choline.

3. A non-aqueous pre-formulation as claimed in claim 1 wherein the organic solvent comprising ethanol is present at a level of 0.1 to 20% by weight.

4. A non-aqueous pre-formulation as claimed in claim 1 wherein the organic solvent comprises ethanol and optionally propylene glycol.

5. A non-aqueous pre-formulation as claimed in claim 1 wherein component c) comprises a mixture of ethanol and an amide, or a mixture of ethanol and a sulfoxide.

6. A non-aqueous pre-formulation as claimed in claim 1 wherein component c) comprises a mixture of ethanol and N-methyl pyrrolidone, or a mixture of ethanol and dimethylsulfoxide.

7. A non-aqueous pre-formulation as claimed in claim 1 which is capable of being dispensed through a needle of 19 awg by manual pressure.

8. A non-aqueous pre-formulation as claimed in claim 1 having a viscosity of 1 to 1000 mPas at 20° C.

9. A method of delivery of a peptide active agent to a human or non-human animal body, said method comprising parenterally administering a non-aqueous pre-formulation of claim 1.

10. A method for the preparation of a depot composition comprising exposing a non-aqueous pre-formulation of claim 1 to an aqueous fluid in vivo.

11. A process for the formation of a non-aqueous pre-formulation according to claim 1 suitable for the administration of a peptide bioactive agent to a subject, said process comprising forming a low viscosity mixture of:
   i) at least one neutral diacyl lipid and/or tocopherol;
   ii) at least one phospholipid;
   iii) at least one biocompatible, organic solvent comprising ethanol;
   and dissolving or dispersing at least one peptide active agent; and at least one lipid soluble acid in the low viscosity mixture, or in at least one of components i) to iii) prior to forming the low viscosity mixture.

12. A pre-filled administration device containing a pre-formulation as claimed in claim 1.

13. A kit comprising an administration device as claimed in claim 12.

14. A non-aqueous pre-formulation comprising a low viscosity mixture of:
   a) 30-70 wt. % of at least one neutral diacyl lipid and/or tocopherol;
   b) 30-60 wt. % of at least one phospholipid c) at least one biocompatible, organic solvent comprising ethanol;
d) at least one GLP-1 receptor agonist; and
e) 0.1-5 wt. % of methane sulfonic acid;
wherein the molar ratio of said peptide active agent to methane sulfonic acid is 1:1 to 1:30;
wherein the pre-formulation forms, or is capable of forming, at least one liquid crystalline phase structure upon contact with an aqueous fluid.

15. A non-aqueous pre-formulation as claimed in claim 14 wherein component a) comprises at least one diacyl glycerol; and component b) comprises at least one phosphatidyl choline.

16. A non-aqueous pre-formulation as claimed in claim 14 wherein the organic solvent comprising ethanol is present at a level of 0.1 to 20% by weight.

17. A non-aqueous pre-formulation as claimed in claim 14 wherein the organic solvent comprises ethanol and optionally propylene glycol.

18. A non-aqueous pre-formulation as claimed in claim 14 wherein component c) comprises a mixture of ethanol and an amide, or a mixture of ethanol and a sulfoxide.

19. A non-aqueous pre-formulation as claimed in claim 14 wherein component c) comprises a mixture of ethanol and N-methyl pyrrolidone, or a mixture of ethanol and dimethylsulfoxide.

20. A non-aqueous pre-formulation as claimed in claim 14 which is capable of being dispensed through a needle of 19 awg by manual pressure.

21. A non-aqueous pre-formulation as claimed in claim 14 having a viscosity of 1 to 1000 mPas at 20° C.

22. A method of delivery of a peptide active agent to a human or non-human animal body, said method comprising parenterally administering a non-aqueous pre-formulation of claim 14.

23. A method for the preparation of a depot composition comprising exposing a non-aqueous pre-formulation of claim 14 to an aqueous fluid in vivo.

24. A pre-filled administration device containing a pre-formulation as claimed in claim 14.

25. A kit comprising an administration device as claimed in claim 24.

* * * * *